US007309688B2

(12) United States Patent
Seiberg et al.

(10) Patent No.: US 7,309,688 B2
(45) Date of Patent: Dec. 18, 2007

(54) TOPICAL ANTI-CANCER COMPOSITIONS AND METHODS OF USE THEREOF

(75) Inventors: Miri Seiberg, Princeton, NJ (US);
Stanley S. Shapiro, Roseland, NJ (US);
Christine Paine, Hoboken, NJ (US);
Allan H. Conney, Princeton, NJ (US);
Mou-Tuan Huang, Englewood Cliffs, NJ (US)

(73) Assignees: Johnson & Johnson Consumer Companies, Skillman, NJ (US);
Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/108,248

(22) Filed: Mar. 27, 2002

(65) Prior Publication Data
US 2003/0064049 A1 Apr. 3, 2003

Related U.S. Application Data

(63) Continuation-in-part of application No. 09/698,454, filed on Oct. 27, 2000.

(51) Int. Cl.
*A01N 37/18* (2006.01)
*A61K 38/00* (2006.01)
*A61K 7/42* (2006.01)
*A61K 9/127* (2006.01)
*A61K 7/00* (2006.01)

(52) U.S. Cl. .......................... 514/2; 424/59; 424/401; 424/450; 424/757; 514/887

(58) Field of Classification Search ............... 424/401, 424/59, 450, 757; 514/2, 887
See application file for complete search history.

(56) References Cited

U.S. PATENT DOCUMENTS

| 3,097,947 | A | 7/1963 | Kemmerer |
|---|---|---|---|
| 3,625,976 | A | 12/1971 | Theimer |
| 3,755,560 | A | 8/1973 | Dickert |
| 4,007,266 | A | 2/1977 | Choay |
| 4,056,637 | A | 11/1977 | Hagiwara et al. |
| 4,151,304 | A | 4/1979 | Evans |
| 4,190,671 | A | 2/1980 | Vanstone |
| 4,219,569 | A | 8/1980 | Glenn |
| 4,223,018 | A | 9/1980 | Belle |
| 4,254,105 | A | 3/1981 | Fukuda |
| 4,272,544 | A | 6/1981 | Cella |
| 4,278,570 | A | 7/1981 | Flom |
| 4,279,930 | A | 7/1981 | Hall |
| 4,297,348 | A | 10/1981 | Frazier |
| 4,331,692 | A | 5/1982 | Drevici |
| 4,333,927 | A | 6/1982 | Ofuchi |
| 4,368,187 | A | 1/1983 | Flom |
| 4,370,315 | A | 1/1983 | Greff |
| 4,382,960 | A | 5/1983 | Flom |
| 4,386,067 | A | 5/1983 | Guillon |
| 4,421,769 | A | 12/1983 | Dixon |
| 4,427,670 | A | 1/1984 | Ofuchi |
| 4,434,095 | A | 2/1984 | Chipens et al. |
| 4,437,895 | A | 3/1984 | Koulbanis |
| 4,439,418 | A | 3/1984 | Moller |
| 4,462,981 | A | 7/1984 | Smith |
| 4,477,434 | A | 10/1984 | Kosaka |
| 4,486,448 | A | 12/1984 | Ser |
| 4,488,564 | A | 12/1984 | Grollier |
| 4,515,778 | A | 5/1985 | Kastell |
| 4,524,067 | A | 6/1985 | Arichi |
| 4,537,782 | A | 8/1985 | Millet |
| 4,550,035 | A | 10/1985 | Smith |
| 4,578,267 | A | 3/1986 | Salamone |
| 4,584,190 | A | 4/1986 | Tejima |
| 4,603,146 | A | 7/1986 | Kligman |
| 4,604,281 | A | 8/1986 | Deckner |
| 4,612,192 | A | 9/1986 | Scheuffgen |
| 4,690,821 | A | 9/1987 | Smith |
| 4,707,293 | A | 11/1987 | Ferro |
| 4,727,088 | A | 2/1988 | Scott et al. |
| 4,760,096 | A | 7/1988 | Sakai |
| 4,793,991 | A | 12/1988 | Slimak |
| 4,824,662 | A | 4/1989 | Hofmann |
| 4,834,076 | A | 5/1989 | Millet |
| 4,847,267 | A | 7/1989 | Deckner |
| 4,851,214 | A | 7/1989 | Walters |
| 4,859,458 | A | 8/1989 | Salamone |
| 4,867,964 | A | 9/1989 | Forestier |
| 4,871,530 | A | 10/1989 | Grollier |
| 4,885,169 | A | 12/1989 | Gazzani |
| 4,895,839 | A | 1/1990 | Bombardelli |
| 4,906,457 | A * | 3/1990 | Ryan ........................ 424/59 |
| 4,943,462 | A | 7/1990 | Komerska |
| 4,960,588 | A | 10/1990 | Hoshowski |
| 4,960,764 | A | 10/1990 | Figueroa |
| 4,970,216 | A | 11/1990 | Deckner |
| 4,971,825 | A | 11/1990 | Kitazume et al. |

(Continued)

FOREIGN PATENT DOCUMENTS

AU 724988 B2 5/1998

(Continued)

OTHER PUBLICATIONS

Sessa et al. "Toasted Soybean Flour Components with Trypsin Inhibitor Activity", JAOCS, vol. 63, No. 6, Jun. 1986, pp. 784-788.*

(Continued)

Primary Examiner—Sreeni Padmanabhan
Assistant Examiner—Kendra D. Carter
(74) Attorney, Agent, or Firm—Dann, Dorfman, Herrell & Skillman; Robert C. Netter

(57) ABSTRACT

Described are skin-care compositions containing non denatured soy products and optionally other anti-cancer or anti-aging agents. The compositions can be applied topically to reduce the risk of UV-induced cutaneous tumors.

15 Claims, 8 Drawing Sheets

U.S. PATENT DOCUMENTS

| | | |
|---|---|---|
| 4,978,528 A | 12/1990 | Degre |
| 5,002,761 A | 3/1991 | Mueller |
| 5,006,337 A | 4/1991 | Motitschke |
| 5,032,382 A | 7/1991 | Crollie |
| 5,032,400 A | 7/1991 | Wiersum |
| 5,043,323 A | 8/1991 | Bombardelli |
| 5,057,417 A | 10/1991 | Hammonds et al. |
| 5,077,038 A | 12/1991 | Hofmann |
| 5,077,040 A | 12/1991 | Bergmann |
| 5,104,655 A | 4/1992 | Bombardelli |
| 5,110,603 A | 5/1992 | Rau |
| 5,116,605 A | 5/1992 | Alt |
| 5,118,671 A | 6/1992 | Bombardelli |
| 5,130,142 A | 7/1992 | Wong et al. |
| 5,147,859 A | 9/1992 | Bombardelli |
| 5,166,139 A | 11/1992 | Bombardelli |
| 5,171,577 A | 12/1992 | Griat |
| 5,179,091 A | 1/1993 | Lesieur |
| 5,188,823 A | 2/1993 | Shapiro |
| 5,192,332 A | 3/1993 | Lang |
| 5,194,252 A | 3/1993 | Hofmann |
| 5,217,717 A * | 6/1993 | Kennedy et al. ............ 424/757 |
| 5,229,104 A | 7/1993 | Sottery |
| 5,231,090 A | 7/1993 | Hsia |
| 5,248,495 A | 9/1993 | Patterson |
| 5,254,331 A | 10/1993 | Mausner |
| 5,260,065 A | 11/1993 | Mathur |
| 5,270,042 A | 12/1993 | Whitham |
| 5,276,058 A | 1/1994 | Satoh |
| 5,306,444 A | 4/1994 | Kitamura |
| 5,310,734 A | 5/1994 | Losch |
| 5,322,839 A | 6/1994 | Voegeli |
| 5,352,443 A | 10/1994 | Kubo |
| 5,362,494 A | 11/1994 | Zysman |
| 5,364,886 A | 11/1994 | Loliger |
| 5,393,519 A | 2/1995 | Dowell |
| 5,397,497 A | 3/1995 | Jakobson |
| 5,407,675 A | 4/1995 | Etemad-Moghadam |
| 5,411,742 A | 5/1995 | Sebag |
| 5,427,814 A | 6/1995 | Loliger |
| 5,428,026 A | 6/1995 | Colarow |
| 5,438,044 A | 8/1995 | Losch |
| 5,439,672 A | 8/1995 | Zabotto |
| 5,443,839 A | 8/1995 | Meybeck |
| 5,443,840 A | 8/1995 | Morancais |
| 5,444,092 A | 8/1995 | Collins |
| 5,446,605 A | 8/1995 | Umehara |
| 5,466,452 A | 11/1995 | Whittle |
| 5,498,420 A | 3/1996 | Mentrup Edgar |
| 5,503,832 A | 4/1996 | De Stoutz |
| 5,505,946 A | 4/1996 | Kennedy et al. |
| 5,510,391 A | 4/1996 | Elson |
| 5,523,308 A | 6/1996 | Costanzo |
| 5,539,129 A | 7/1996 | Zysman |
| 5,545,399 A | 8/1996 | Lee |
| 5,547,661 A | 8/1996 | Sun |
| 5,554,647 A | 9/1996 | Perricone |
| 5,565,439 A * | 10/1996 | Piazza et al. ............... 514/110 |
| 5,565,493 A | 10/1996 | Nakata et al. |
| 5,567,420 A | 10/1996 | McEleney |
| 5,569,663 A | 10/1996 | Ribier |
| 5,571,503 A | 11/1996 | Mausner |
| 5,578,297 A | 11/1996 | Mellul |
| 5,589,181 A | 12/1996 | Bencsits |
| 5,595,984 A | 1/1997 | Blank |
| 5,597,814 A | 1/1997 | Blank |
| 5,601,833 A | 2/1997 | Roboer |
| 5,603,949 A | 2/1997 | Meybeck |
| 5,605,894 A | 2/1997 | Blank |
| 5,607,666 A | 3/1997 | Masson . |
| 5,607,692 A | 3/1997 | Ribier |
| 5,614,180 A | 3/1997 | Chung |
| 5,614,215 A | 3/1997 | Ribier |
| 5,616,572 A | 4/1997 | Blank |
| 5,618,522 A | 4/1997 | Kaleta |
| 5,620,692 A | 4/1997 | Potter |
| 5,622,690 A | 4/1997 | Potter |
| 5,626,868 A | 5/1997 | Morancais |
| 5,629,015 A | 5/1997 | Ribier |
| 5,629,301 A | 5/1997 | Blank |
| 5,631,318 A | 5/1997 | Ito |
| 5,635,165 A | 6/1997 | Panitch |
| 5,637,316 A | 6/1997 | Ribier |
| 5,639,785 A | 6/1997 | Kung |
| 5,641,509 A | 6/1997 | Gross |
| 5,643,583 A | 7/1997 | Voultoury |
| 5,643,587 A | 7/1997 | Scancarella |
| 5,643,601 A | 7/1997 | Gross |
| 5,650,166 A | 7/1997 | Ribier |
| 5,652,230 A | 7/1997 | Blank |
| 5,653,988 A | 8/1997 | Gerber |
| 5,660,853 A | 8/1997 | Hansenne-Richoux |
| 5,665,367 A | 9/1997 | Burger |
| 5,670,547 A | 9/1997 | Milstein et al. |
| 5,674,511 A | 10/1997 | Kacher |
| 5,676,935 A | 10/1997 | Mellul |
| 5,676,956 A | 10/1997 | Duffy |
| 5,679,374 A | 10/1997 | Fanchon |
| 5,681,571 A | 10/1997 | Homgren et al. |
| 5,681,852 A | 10/1997 | Bissett |
| 5,683,683 A | 11/1997 | Scafidi |
| 5,686,102 A | 11/1997 | Gross |
| 5,688,763 A | 11/1997 | Hammonds, Jr. et al. |
| 5,691,327 A | 11/1997 | Blank |
| 5,712,356 A | 1/1998 | Bothe et al. |
| 5,723,148 A | 3/1998 | Love |
| 5,741,496 A | 4/1998 | Khaiat |
| 5,753,612 A | 5/1998 | Mitrani |
| 5,755,814 A | 5/1998 | Berg |
| 5,762,916 A | 6/1998 | Ansmann |
| 5,766,628 A | 6/1998 | Nurnberg |
| 5,776,917 A | 7/1998 | Blank |
| 5,780,456 A | 7/1998 | Blank |
| 5,780,457 A | 7/1998 | Blank |
| 5,780,458 A | 7/1998 | Blank |
| 5,780,459 A | 7/1998 | Blank |
| 5,786,345 A | 7/1998 | Blank |
| 5,786,346 A | 7/1998 | Blank |
| 5,789,396 A | 8/1998 | Blank |
| 5,795,879 A | 8/1998 | Blank |
| 5,801,163 A | 9/1998 | Blank |
| 5,804,216 A | 9/1998 | Terren |
| 5,807,545 A | 9/1998 | Coffindaffer |
| 5,811,119 A | 9/1998 | Mehta et al. |
| 5,824,702 A | 10/1998 | Wei |
| 5,833,965 A | 11/1998 | Sun |
| 5,834,013 A | 11/1998 | Ribier |
| 5,840,717 A | 11/1998 | Blank |
| 5,843,907 A | 12/1998 | Sakai et al. |
| 5,843,926 A | 12/1998 | Blank |
| 5,863,546 A | 1/1999 | Swinehart |
| 5,869,470 A | 2/1999 | Blank |
| 5,871,743 A | 2/1999 | Chajuss |
| 5,871,823 A | 2/1999 | Anders et al. |
| 5,880,314 A | 3/1999 | Shinomiya |
| 5,885,593 A | 3/1999 | Epstein |
| 5,885,596 A | 3/1999 | Parab |
| 5,885,600 A | 3/1999 | Blum |
| 5,885,617 A | 3/1999 | Jordan |
| 5,885,948 A | 3/1999 | Glenn |
| 5,888,522 A | 3/1999 | Pickart |
| 5,908,618 A | 6/1999 | Lorant |
| 5,912,175 A | 6/1999 | Wille, Jr. |
| 5,916,577 A | 6/1999 | Golz |

| Patent Number | | Date | Inventor |
|---|---|---|---|
| 5,928,654 | A | 7/1999 | Duranton |
| 5,928,658 | A | 7/1999 | Kishida |
| 5,928,889 | A | 7/1999 | Bakich |
| 5,936,052 | A | 8/1999 | Bothe et al. |
| 5,942,479 | A | 8/1999 | Frankenbach |
| 5,945,095 | A | 8/1999 | Mougin |
| 5,945,109 | A | 8/1999 | Schmidt |
| 5,952,373 | A | 9/1999 | Lanzendorfer |
| 5,958,387 | A | 9/1999 | Bara |
| 5,961,980 | A | 10/1999 | Kennedy |
| 5,962,015 | A | 10/1999 | Delrieu et al. |
| 5,962,414 | A | 10/1999 | Birk |
| 5,962,441 | A | 10/1999 | Blank |
| 5,965,153 | A | 10/1999 | Allen |
| 5,972,355 | A | 10/1999 | Knight et al. |
| 5,981,450 | A | 11/1999 | Fabry |
| 5,985,338 | A | 11/1999 | Suh |
| 5,985,809 | A | 11/1999 | Frankenback |
| 5,990,291 | A | 11/1999 | Waggle |
| 6,004,558 | A | 12/1999 | Thurn et al. |
| 6,004,915 | A | 12/1999 | Elliott |
| 6,013,250 | A | 1/2000 | Cannell |
| 6,013,255 | A | 1/2000 | Edens |
| 6,017,549 | A | 1/2000 | Knight et al. |
| 6,017,893 | A | 1/2000 | Segelman |
| 6,018,001 | A | 1/2000 | Hiratani et al. |
| 6,019,962 | A | 2/2000 | Rabe |
| 6,030,931 | A | 2/2000 | Vinski |
| 6,033,680 | A | 3/2000 | Dixon |
| 6,045,779 | A | 4/2000 | Mueller |
| 6,048,520 | A | 4/2000 | Hoshowski |
| 6,051,602 | A | 4/2000 | Bissett |
| 6,054,137 | A | 4/2000 | Breton |
| 6,060,070 | A | 5/2000 | Gorbach |
| 6,063,398 | A | 5/2000 | Gueret |
| 6,080,393 | A | 6/2000 | Liu et al. |
| 6,093,411 | A | 7/2000 | Bissett |
| 6,096,327 | A | 8/2000 | Lezdey et al. |
| 6,126,933 | A * | 10/2000 | Warne et al. ............... 424/85.2 |
| 6,180,662 | B1 | 1/2001 | Lanzendorfer |
| 6,183,761 | B1 | 2/2001 | Bissett |
| 6,183,762 | B1 | 2/2001 | Deckers et al. |
| 6,248,350 | B1 | 6/2001 | Mori et al. |
| 6,261,603 | B1 | 7/2001 | McElwain |
| 6,323,219 | B1 * | 11/2001 | Costanzo ................... 514/317 |
| 6,399,083 | B1 | 6/2002 | Pillai et al. |
| 6,433,025 | B1 | 8/2002 | Lorenz |
| 6,447,809 | B1 | 9/2002 | Krumhar et al. |
| 6,558,656 | B2 | 5/2003 | Mann |
| 6,689,582 | B1 * | 2/2004 | Davies et al. ............... 435/69.1 |
| 2002/0065300 | A1 | 5/2002 | Seiberg et al. |
| 2002/0160061 | A1 | 10/2002 | Saliou et al. |
| 2002/0160062 | A1 | 10/2002 | Liu et al. |
| 2002/0160063 | A1 | 10/2002 | Miller et al. |
| 2002/0192313 | A1 | 12/2002 | Saliou et al. |
| 2002/0197244 | A1 | 12/2002 | Seiberg et al. |
| 2003/0064048 | A1 | 4/2003 | Seiberg et al. |
| 2003/0224075 | A1 | 12/2003 | Liu et al. |
| 2004/0009142 | A1 | 1/2004 | Zambaux et al. |
| 2004/0063593 | A1 | 4/2004 | Wu et al. |

FOREIGN PATENT DOCUMENTS

| | | |
|---|---|---|
| CN | 1081899 | 2/1994 |
| CN | 1094279 A | 11/1994 |
| CN | 1146876 | 4/1997 |
| CN | 1166960 | 12/1997 |
| DE | 4432947 | 3/1996 |
| DE | 19634206 | 3/1998 |
| DE | 19818849 A | 10/1998 |
| EP | 0 273 202 A2 | 7/1988 |
| EP | 0 341 745 A1 | 11/1989 |
| EP | 0 393 532 A2 | 10/1990 |
| EP | 0 421 021 A1 | 4/1991 |
| EP | 0 473 502 A1 | 3/1992 |
| EP | 0 476 311 A1 | 3/1992 |
| EP | 0 508 886 A1 | 10/1992 |
| EP | 301122 B1 * | 10/1992 |
| EP | 0 574 352 A1 | 12/1993 |
| EP | 581624 | 2/1994 |
| EP | 582239 | 2/1994 |
| EP | 0 643 083 A1 | 3/1995 |
| EP | 0 643 960 A1 | 3/1995 |
| EP | 0 655 470 A1 | 5/1995 |
| EP | 0 661 037 A1 | 7/1995 |
| EP | 0 707 851 A2 | 4/1996 |
| EP | 0 713 106 A1 | 5/1996 |
| EP | 0 758 687 A1 | 2/1997 |
| EP | 0 774 249 A2 | 5/1997 |
| EP | 0 811 595 A1 | 12/1997 |
| EP | 0 814 116 A1 | 12/1997 |
| EP | 0 963 761 A1 | 12/1999 |
| EP | 1 074 240 A2 | 2/2001 |
| EP | 1 077 063 A2 | 2/2001 |
| EP | 1 192 938 A2 | 4/2002 |
| EP | 1 210 946 A | 6/2002 |
| EP | 1 236 402 A2 | 9/2002 |
| EP | 1 236 465 A2 | 9/2002 |
| FR | 2 596 986 A1 | 10/1987 |
| FR | 2 641 696 A1 | 7/1990 |
| FR | 2 685 202 A1 | 6/1993 |
| FR | 2 803 747 A1 | 7/2001 |
| FR | 2 811 226 A1 | 1/2002 |
| JP | 58225003 A | 12/1983 |
| JP | 58225004 A | 12/1983 |
| JP | 59187756 A | 10/1984 |
| JP | 60061513 | 4/1985 |
| JP | 62036304 A | 2/1987 |
| JP | 63068512 A | 3/1988 |
| JP | 63096120 A | 4/1988 |
| JP | 63227515 A | 9/1988 |
| JP | 63316711 A | 12/1988 |
| JP | 1096106 A | 4/1989 |
| JP | 3127713 A | 5/1991 |
| JP | 4169514 A | 6/1992 |
| JP | 04283518 | 10/1992 |
| JP | 5015574 A | 1/1993 |
| JP | 5114905 A | 5/1993 |
| JP | 5213729 A | 8/1993 |
| JP | 5246932 A | 9/1993 |
| JP | 5320024 A | 12/1993 |
| JP | 5320061 A | 12/1993 |
| JP | 6145061 A | 5/1994 |
| JP | 6192085 A | 7/1994 |
| JP | 7010772 A | 1/1995 |
| JP | 7196527 A | 8/1995 |
| JP | 7196529 A | 8/1995 |
| JP | 7304655 A | 11/1995 |
| JP | 8012560 A | 1/1996 |
| JP | 8020597 A | 1/1996 |
| JP | 8040824 A | 2/1996 |
| JP | 8059450 A | 3/1996 |
| JP | 8099891 A | 4/1996 |
| JP | 8143442 A | 6/1996 |
| JP | 8333260 A | 12/1996 |
| JP | 9025212 A | 1/1997 |
| JP | 9025214 A | 1/1997 |
| JP | 9059166 A | 3/1997 |
| JP | 9077638 A | 3/1997 |
| JP | 9176033 A | 7/1997 |
| JP | 410226642 | 8/1998 |
| JP | 11346695 A | 12/1999 |
| JP | 2000302678 A | 10/2000 |
| KR | 92-8851 B1 | 10/1992 |
| KR | 92-8853 B | 10/1992 |
| RU | 2066992 C1 | 9/1996 |

| | | |
|---|---|---|
| WO | WO 87/07838 A1 | 12/1987 |
| WO | WO 91/04283 A1 | 4/1991 |
| WO | WO 91/07166 A1 | 5/1991 |
| WO | WO 92/09639 A2 | 6/1992 |
| WO | WO 92/09650 A1 | 6/1992 |
| WO | WO 94/06485 A1 | 3/1994 |
| WO | WO 95/04609 A1 | 2/1995 |
| WO | WO 95/09002 A1 | 4/1995 |
| WO | WO 95/09011 A1 | 4/1995 |
| WO | WO 95/24885 A1 | 9/1995 |
| WO | WO 96/09806 A2 | 4/1996 |
| WO | WO 96/19483 A1 | 6/1996 |
| WO | WO 96/19491 A1 | 6/1996 |
| WO | WO 96/24371 A1 | 8/1996 |
| WO | WO 96/24392 A1 | 8/1996 |
| WO | WO 96/30035 A1 | 10/1996 |
| WO | WO 96/30396 A1 | 10/1996 |
| WO | WO 96/31194 A2 | 10/1996 |
| WO | WO 96/37497 A1 | 11/1996 |
| WO | WO 96/40121 A1 | 12/1996 |
| WO | WO 96/40199 A1 | 12/1996 |
| WO | WO 97/11033 A2 | 3/1997 |
| WO | WO 97/18904 A1 | 5/1997 |
| WO | WO 97/35998 A1 | 10/1997 |
| WO | WO 97/39733 A1 | 10/1997 |
| WO | WO 98/01107 A1 | 1/1998 |
| WO | WO 98/02134 A1 | 1/1998 |
| WO | WO 98/02138 A1 | 1/1998 |
| WO | WO 98/05333 A1 | 2/1998 |
| WO | WO 98/08503 A1 | 3/1998 |
| WO | WO 98/09987 A1 | 3/1998 |
| WO | WO 98/17246 A1 | 4/1998 |
| WO | WO 98/33089 A1 | 7/1998 |
| WO | WO 98/49153 A1 | 11/1998 |
| WO | WO 9900110 | 1/1999 |
| WO | WO 99/04752 | 2/1999 |
| WO | WO 99/04752 A2 | 2/1999 |
| WO | WO 99/09065 A1 | 2/1999 |
| WO | WO 99/15917 A1 | 4/1999 |
| WO | WO 99/24003 A1 | 5/1999 |
| WO | WO 99/30729 A1 | 6/1999 |
| WO | WO 99/36050 A1 | 7/1999 |
| WO | WO 9939682 | 8/1999 |
| WO | WO 99/57178 A1 | 11/1999 |
| WO | WO 00/15188 A1 | 3/2000 |
| WO | WO 00/43049 A1 | 7/2000 |
| WO | WO 00/51554 A2 | 9/2000 |
| WO | WO 00/62740 A2 | 10/2000 |
| WO | WO 00/62741 A2 | 10/2000 |
| WO | WO 00/62743 A2 | 10/2000 |
| WO | WO 00/62744 A2 | 10/2000 |
| WO | WO 00/62745 A2 | 10/2000 |
| WO | WO 00/69404 A1 | 11/2000 |
| WO | WO 00/69406 A1 | 11/2000 |
| WO | WO 00/69407 A1 | 11/2000 |
| WO | WO 00/69408 A1 | 11/2000 |
| WO | WO 01/34099 A1 | 5/2001 |
| WO | WO 01/35920 A1 | 5/2001 |
| WO | WO 02/07697 A1 | 1/2002 |
| WO | WO 02/067988 | 9/2002 |

OTHER PUBLICATIONS

Odani et al., "Studies on Soybean Trypsin Inhibitors", J. Biochem, vol. 83, No. 3, 1978, pp. 747-753.*
Mukhopadhyay, "The molecular evolutionary history or a winged bean alpha-chymotrypsin inhibitor and modeling of its mutations through structural analyses", Journal of Molecular Evolution, Mar. 2000, vol. 50, No. 3, pp. 214-223.*
U.S. Appl. No. 10/611,100, filed Jul. 1, 2003, Halas et al.
U.S. Appl. No. 09/110,409, filed Jul. 6, 1998, Seiberg et al.
U.S. Appl. No. 10/659,598, filed Sep. 10, 2003, Seiberg et al.
U.S. Appl. No. 09/206,249, filed Dec. 7, 1998, Seiberg et al.
U.S. Appl. No. 09/677,511, filed Sep. 29, 2000, Liu et al.
U.S. Appl. No. 09/621,565, filed Jul. 20, 2000, Seiberg et al.
U.S. Appl. No. 10/434,309, filed May 8, 2003, Seiberg et al.
"A Combined Soybean Crushing-Deodorizing System that Yields 100-200 Mesh Powder for Food Additive Use has been Developed by Shinyu Zoki Co. Ltd. And Mitsubishi Rayon Engineering Ltd.", *Tech Times*, pp. 10 (1978).
"Avon's Anew Positivity Trio Targets Menopausal Women", The Rose Sheet, Feb. 28, 2000, p. 8.
"CaspACE™ Assay System, Colorimetric", Product Improvements, Neural Notes vol. V, Issue 1, p. 13 (1999) Promega Corporation.
"Elhibin®" Product Brochure, PENTAPHARM, Centerchem, Inc., Stamford, CT, publicly available prior to Feb. 28, 2001.
"EnzChek® Protease Assay Kits" Product Information, MP06638, pp. 1-4, Revised Feb. 25, 2001, Molecular Probes, Eugene, OR.
"Flavosterone S (Soybean Extract Contained Iso-Flavone", Ichimaru Pharcos Co., Ltd. pp. 11-13 (Dec. 22, 1998).
"Isoral" Soybean power makes your skin clear and moist!—Brochure, publicly available prior to Feb. 28, 2001.
"Lipoxydase Code 411784", Lipoxydase File Apr. 1999, A LlBiol Body Care Composition.
"Nudit Advertisement", publicly available prior to Feb. 28, 2001.
"Patent Abstracts—Gastric Juice for Antiaging 1997".
"Patent Abstracts—Plant extracts for skin Whitening", publicly available prior to Feb. 28, 2001.
"Patent Abstracts—Soybeans for skin pigmentation 1997".
"Patent Abstracts—Soybeans for skin whitening 1997".
"Patent Abstracts of requested patent titles 1996".
"Patent List—Thrombin Inhibitors: List of Relevant Patent Applications as of Jul. 8, 1998, and Oct. 1, 1996."
"Plant Extract Containing Female Hormone-Like Isoflavones—Flavosterone", leaflet from Ichimaru Pharcos issued Mar. 7, 1997.
"Product for Damaged hair by Bristol-Myers-Squibb", (Abstract) publicly available prior to Feb. 28, 2001.
"RQ1 RNase-Free DNASE", Promega Corporation, Technical Bulletin No. 518, pp. 1-4, Feb. 2000, Part#TB518, Promega Corporation, 2800 Woods Hollow Rd., Madison, WI 53711-5399.
"Soy Protein Prevents Skin Tumors From Developing in Mice", *Gene Therapy Weekly*, ISSN 1078-2842, pp. 21 (Nov. 8, 2001).
"Soy Therapy", www.wiseessentials.com/soytherapy.html (email from Jue-Chen Liu, Ph.D. to Cunero et al dated Apr. 13, 2000) Wise Essentials.
"Soybean Technology Improves Skin", *Allured's Cosmetics & Toiletries Magazine*, vol. 115, No. 3, Mar. 2000, p. 22.
"Superscript II Reverse Transciptase" protocol published by Gibco-BRL (now Life Tech Inc.) Apr. 1992.
"The Joy of Soy", www.wheat-grass.com/851_oral_liquid.shtml, Wheatgrass Express, Inc., 1996.
"ThermoScript™ RNase H-Reverse Transcriptase", Invitrogen™ Life Technologies, www.invitrogen.com/content.cfm, Invitrogen Corporation, 2001.
"Whitening with Soybean? HR has launched "Future White" in Japan", Helena Rubinstein, publicly available prior to Feb. 28, 2001.
Ahrens et al, "Photocarcinogenesis and Inhibition of Intercellular Adhesion Molecular I Expression in Cells of DNA-Repair-Defective Individuals", *Proc. National Academy of Sciences*, vol. 94 (1997) pp. 6837-6841.
Badash et al, "Effect of Gamma Irradiation of Field and Storage Fungi of Wheat, Maize and Soybean", *Chemie Mikrobiologie Technologie die Lebensmittel* (1992).
Balsam et al, *Cosmetics, Science and Technology*, 2nd Edition, vol. 1, pp. 32-43 (1972).
Balsam et al, *Cosmetics, Science and Technology*, 2nd Edition, vol. 1, pp. 72-73 (1972).
Barbuch et al, "The Use of Thermospray Liquid Chromatography/Tandem Mass Spectrometry for the Class Identification and Structural Verification of Phytoestrogens in Soy Protein Preparations", *Biomedical and Environmental Mass Spectrometry*, vol. 18 (1989) pp. 973-977.

Barel et al, "Suction Method for Measurement of Skin Mechanical Properties: The Cutometer®", Chapter 14.3, pp. 335-340, Handbook of Non-Invasive Methods and the Skin, Jorgen Serup and G.B.E. Jemec (1995).

Batista et al, "Primary Structure of a Kunitz-Type Trypsin Inhibitor From Enterolobium Contortisiliquum Seeds", Phytochemistry, vol. 41, No. 4, (1996) pp. 1017-1022.

Benshimol, "The Biochemistry And Nutrition Group: 30 Years Of Research In A Developing Country", Archivos LatinoAmericanos De Nutrician, vol. 44, No. 4-S, pp. 6-S-9-S (1994).

Billings et al, "A Growth-Regulated Protease Activity that is inhibited by the Anticarcinogenic Bowman-Birk Protease Inhibitor", Pro. Natl. Acad. Sci., vol. 89, pp. 3120-3124 (1992).

Birk, "Protein Proteinase Inhibitors in Legume Seeds—Overview", Archivos Latinoamericanos de Nutricion, vol. 44, No. 4-S (1994) pp. 26-S-30-S.

Birk, "The Bowman-Birk Inhibitor—Trypsin- and Chymotrypsin-Inhibitor from Soybeans", Int. J. Peptide Protein Res., vol. 25, pp. 113-131 (1985).

Blackheart et al, "Ligand Cross-Reactivity Within the Protease-Activated Receptor Family", The Journal of Biological Chemistry, vol. 271, No. 28, pp. 16466-16471 (1996).

Bonifacino et al, "Electrophoresis and Immunoblotting", Chapter 6, pp. 6.0.1-6.6.1, Current Protocols in Cell Biology, copyright 2000 by John Wiley & Sons, Inc.

Brass et al, "Protease-Activated G Protein Coupled Receptors On Human Platelets and Endothelial Cells", F.K. Schattauer Verlagsgesellschaft mbH (Stuttgart, vol. 78, No. 1, pp. 234-241 (1997).

Chomczynski et al, "Single-Step Method of RNA Isolation by Acid Guanidinium Thiocyanate-Phenol-Chloroform Extraction," Analytical Biochemistry, vol. 162, pp. 156-159 (1987).

Clark et al, "Tryptase Inhibitors Block Allergen-induced Airway and Inflammatory Responses in Allergic Sheep", American Journal of Respiratory and Critical Care Medicine, vol. 152, pp. 2076-2083, 1995.

Connor et al, "Depletion of Cutaneous Glutathione By Ultraviolet Radiation", Photochemistry and Photobiology, vol. 46, No. 2, pp. 239-245 (1987).

Costanzo et al, "Potent Thrombin Inhibitors That Probe The S1 Subsite: Tripeptide Transition State Analogues Based On A Heterocycle Activated Carbonyl Group", J. Med. Chem., vol. 39, 1996, pp. 3039-3043.

Couglin, "Protease Activated Receptors Start A Family", Proc. Natl. Acad. Sci. USA, vol. 91, 1994, pp. 9200-9202.

Covelli et al, "Diazepam Inhibits Phagocytosis and Killing Exerted By Polymorphonuclear Cells and Monocytes From Healthy Donors", Abstract, Immunopharmacology and Immunotoxicology, vol. 11, No. 4 (1989) pp. 701-714, copyright © 1989 by Marcel Dekker, Inc.

Cunniff, "Official Methods of Anaysis of AOAC International", 16th Adition, 5th Revision (1999) AOAC International.

De Seidl, "Interaction of Proteases with Legume Seed Inhibitors, Molecular Features", Archivos Latinoamericanos de Nutricon, vol. 44, No. 4-S (1994) pp. 21-S-25-S.

Derian et al, "Differential Regulation of Human Keratinocyte Growth and Differentiation by a Novel Family of Protease-activated Receptors"; Cell Growth & Differentiation, vol. 8, pp. 743-749, Jul. 1997.

Dewitt et al, "Astrocytes Regulate Microglial Phagocytosis Of Senile Plaque Cores Of Alzheimer's Disease", Experimental Neurology, vol. 149, Article No. EN976738 (1998) pp. 329-340.

Doolittle, "Proteins", Reading from Scientific American—The Molecules of Life, Chapter 4, pp. 38-47 (1985).

Doring, "The Role Of Neutrophil Elastase In Chronic Inflammation", American Journal of Respiratory and Critical Care Medicine, vol. 150, 1994, pp. S114-S117.

Dunaevsky et al, "Two Groups of Protease Inhibitors Functionally Active in Buckwheat Seeds", soba.shinshu-uac.jp/contents/105.html, publicly available prior to Feb. 28, 2001.

Dunaevsky et al, "Isolation and Properties of Anionic Protease Inhibitors from Buckwheat Seeds", Biochemistry and Molecular Biology International, vol. 40, No. 1, (Sep. 1996) pp. 199-208.

Ebling et al, "Hair", Journal of Investigative Dermatology, vol. 67, No. 1, pp. 98-105 (Jul. 1976).

Ebling, "Hair Follicles and Associated Glands as Androgen Targets", Clinics in Endocrinology and Metabolism, vol. 15, No. 2, pp. 319-339 (May 1986).

Fagerholm et al, "The Effect of a Drug-delivery System Consisting of Soybean Phosphatidyl Choline and Medium-chain Monoacylglycerol on the Intestinal Permeability of Hexarelin in the Rat", J. Pharm. Pharmacol. (1998) vol. 50, pp. 467-473.

Fimiani et al, "Mid-Dermal Elastolysis; An Ultrastructural and Biochemical Study", Arch. Dermatol Res., vol. 287, (1995) pp. 152-157.

Fox et al, "Identification Of Potential Activators Of Proteinase-Activated Receptor-2", Federation of European Biochemical Societies, FEBS Letters 417 (1997) pp. 267-269.

Galvez et al, "Chemopreventive Property of a Soybean Peptide (Lunasin) That Binds to Deacetylated Histones and Inhibits Acetylation", Cancer Research, vol. 61, No. 20, pp. 7473-7478 (Oct. 15, 2001).

Grant-Theule, "Periodontal Disease, Diabetes, and Immune Response: A Review Of Current Concepts", Peridontal Abstracts, vol. 44, No. 3, 1996, pp. 69-77.

Greenberger, "Immunologic Aspects Of Lung Diseases And Cystic Fibrosis", JAMA, vol. 278, No. 22 (1997) pp. 1924-1930.

Guo et al, "A Serine Protease From Suspension-Cultured Soybean Cells", Phytochemistry, vol. 47, No. 4 (1998) pp. 547-553.

Hachimi et al, "Do Microglial Cells Phagocyte The B/A4-Amyloid Senile Plaque Core of Alzheimer Disease?", C.R. Academy of Science, Paris, Sciences de la vie/Life sciences, vol. 317, 1994, pp. 445-451.

Hacker, "Common Disorders Of Pigmentation—When are more than cosmetic cover-ups required?", Postgraduate Medicine, vol. 99, No. 6, 1996, pp. 177-186.

Hafez et al, "Effects of Gamma Irradiation on Proteins and Fatty Acids of Soybean", Journal of Food Science, vol. 50 (1985) pp. 1271-1274.

Hamada, "Evaluation of the Effects of Hair Re-growth Agents on Lengthening the Anagen Phase Period and Blockage of Anagen phase-Catagen phase Transformation", J. Soc. Cosmet. Chem. Japan, vol. 31, No. 4 (1997) pp. 413-419.

Hanada et al, "Photoprotective Effect of Esterified Glutathione Against Ultraviolet B-Induced Sunburn Cell Formation in the Hairless Mice", The Journal of Investigative Dermatology, vol. 108, No. 5, pp. 727-730 (1997).

Hasler et al, "Nutrition Communique, Soy: Just a Hill of Beans?", Journal of Women's Health, vol. 7, No. 5 (1998) pp. 519-523.

Hattori et al, "Effects of sup.60 Co- gamma-rays on Defatted Soybean Powder", Food Irradiation, vol. 3, No. 1, pp. 104-110 (1968).

Hayashi et al, "Inhibition of Serine Proteases of the Blood Coagulation System by Squash Family Protease Inhibitors", J. Biochem., vol. 116, No. 5, pp. 1013-1018 (1994).

Hendrich et al, "Defining Food Components as New Nutrients", American Institute of Nutrition, Food Composition (1994) pp. 1789S-1792S.

Hoff et al, "Macrophage Uptake Of Cholesterol-Containing Particles Derived From LDL and Isolated From Atherosclerotic Lesions", European Heart Journal, vol. 11, Supplement E, 1990, pp. 105-115.

Hollenberg et al, "Proteinase-Activated Receptor-2 in Rat Aorta: Structural Requirements for Agonist Activity of Receptor-Activating Peptides", Molecular Pharmacology, vol. 49, pp. 229-233 (1996).

Itami et al, "Mechanism of Action of Androgen in Hair Follicles", Journal of Dermatological Science, 7 Suppl., S98-S103 (Jul. 1994).

Jimenez et al, "Mammalian Tyrosinase: Biosynthesis, Processing and Modulation By Melanocyte Stimulating Hormone", Proc. Natl. Acad. Sci. USA (1988), vol. 85, pp. 3830-3834.

Jimenez et al, "Specific Identification of an Authentic Clone for Mammalian Tyrosinase", The Journal of Biological Chemistry, (1989) vol. 264, No. 6, pp. 3397-3403.

Jingtian et al, "Studies of Soy Sauce Sterlization and its Special Flavour Improvement by Gamma-Ray Irradiation", *Radiation Physics and Chemistry*, vol. 31, Nos. 1-3, pp. 209-213 (1988).

Keeton et al, "The Chemistry of Life", *Biological Science*, Fourth Edition, Chapter 3, pp. 66-67 (1986).

Kennedy et al, "Prevention of Carcinogenesis by Protease Inhibitors", *Cancer Research*, vol. 54, No. 7 (suppl), pp. 1999s-2005s (Apr. 1, 1994).

Kennedy, "The Evidence for Soybean Products as Cancer Preventive Agents", *The Journal of Nutrition*, vol. 125, No. 3 Suppl, pp. 733s-743s (Mar. 1995).

Kennedy, "Chemopreventive Agents: Protease Inhibitors," *Pharmacol. Ther.*, vol. 78, No. 3, pp. 167-209, copyright 1998 Elsevier Science Inc.

Kennedy, "The Bowman Birk Inhibitor from Soybeans As An Anticarcinogenic Agent", *American Journal of Clinical Nutrition*, vol. 68(suppl), pp. 1406S-1412S (1998).

Kovacs et al, "Effect of Irradiation and Dielectric Heating on Soybean Ultrastructure, Trypsin Inhibitor, and Lipoxygenase Activities", *Food Structure*, vol. 10, pp. 217-227 (1991).

Lam et al, "Combined Effect of Irradiation and Dielectric Heating on Chemical Properties of Soybeans", *7th Symp. On Radiation Chemistry*, pp. 477-483 (1990).

Limtrakul et al, "Suppressive Effect of Soybean Milk Protein on Experimentally Induced Skin Tumor in Mice", *Life Sciences*, vol. 53 (1993) pp. 1591-1596.

Liu et al, "Aqueous Ethanol Extraction of Soybean Trypsin Inhibitors and Characterization of a Calcium-Sensitive Fraction", *Journal of Food Biochemistry*, vol. 15 (1991) pp. 159-168.

Liu, "Chemistry And Nutritional Value Of Soybean Components", in *Soybeans, Chemistry Technology and Utilization*, pp. 32-35 (copyright © 1997 by Chapman & Hall).

MacFarlane et al, "Refractory Periodontitis Associated With Abnormal Polymorphonuclear Leukocyte Phagocytosis and Cigarette Smoking", *J. Peridontal*, vol. 63, No. 11, Nov. 1992, pp. 908-913.

Maes et al, "Leukocytosis, Monocytosis and Neutrophilla: Hallmarks Of Severe Depression", *J. Psychiat. Res.*, vol. 26, No. 2 (1992) pp. 125-134.

Mahoney et al, "Amino Acid Sequence and Secondary Structural Analysis of the Corn Inhibitor of Trypsin and Activated Hageman Factor", *Journal of Biological Chemistry*, vol. 259, No. 13 (Jul. 10, 1984) pp. 8412-8416.

McAdams et al, "Neutrophil and Monocyte Phagocytosis in Depressed Patients", *Prog. Neuro-Psychopharmacol & Biol. Psychiat* (1993) vol. 17, pp. 971-984.

McCutcheon's Emulsifiers and Detergents 1986, North American Edition, McCutcheon Division, Mc Publishing Co., Glen Rock, New Jersey, pp. 317-324 (1986).

Meister, "Glutathione, Ascorbate, and Cellular Protection", *Cancer Research*, vol. 54, pp. 1969s-1975s (1994).

Merck Index (12th Edition), Edited by Susan Budavari (1996) Thrombin., entry 9525, p. 1601.

Merck Index (12th Edition), Edited by Susan Budavari (1996) Trypsin, entry 9926, p. 1669.

Mercola, "Concerns Regarding Soybeans", www.rheumatic.org/soy.htm, publicly available prior to Feb. 28, 2001.

Messina, "Soy Intake and Cancer Risk: A Review of the In Vitro and In Vivo Data", *Nutrician and Cancer*, vol. 21, No. 2 (1994) pp. 113-131.

Mezei et al, "Liposomes-A Selective Drug Delivery System for the Topical Route of Administration: Gel Dosage Form", Journal of Pharmaceutics and Pharmacology, vol. 34 (1982), pp. 473-474.

Mezei, "Liposomes as a Skin Drug Delivery System", *Topics in Pharmaceutical Sciences* (D. D. Breimer and P. Speiser, eds.,), Elsevier Science Publishers B. V., New York, N.Y., 1985, pp. 345-358.

Miyagi et al, "Trypsin Inhibitor Activity in Commercial Soybean Products in Japan", *J. Nutr. Sci. Vitaminol* (1997) vol. 43, pp. 575-580.

Molinari et al, "Inhaled Tryptase Causes Bronchoconstriction in Sheep Via Histamine Release", *American Journal of Respiratory and Critical Care Medicine*, vol. 154, pp. 649-653, 1996.

Molino et al, "Interactions of Mast Cell Tryptase with Thrombin Receptors and PAR-2", *Journal of Biological Chemistry*, vol. 272, No. 7, Feb. 14, 1997, pp. 4043-4049.

Morita et al, "Partial Purification and Characterization of a Novel Soybean Protease Which is Inhibited by Kunitz and Bowman-Birk Trypsin Inhibitors", *J. Biochem.*, vol. 119, No. 4, 1996, pp. 711-718.

Mulimani et al, "Effect of Heat Treatments on Trypsin/Chyomotrypsin Inhibitor Activity of Red Gram (Cajanus Cajan L.)", *Plant Foods for Human Nutrition*, vol. 46, No. 2, (1994) pp. 103-107.

Mulimani et al, "Effects Of Heat Treatment and Germination On Trypsin and Chymotrypsin Inhibitory Activities in Sorghum (Sorghum Bicolor (L.) Moench) Seeds", *Plant Foods for Human Nutrition*, vol. 44, No. 3 (1993) pp. 221-226.

Murphy, "Phytoestrogen Content of Processed Soybean Products", *Food Technology*, vol. 1, pp. 60-64 (1982).

Musclow et al., "Fluorescence Assay To Monitor Phagocytosis By Blood-Clot Derived Polymorphonuclear Leucocytes, 1 Study Of Patients With Diabetes And Phagocytosis Of Different Staphyloccoccal Species", *Cytobios*, vol. 65, 1991, pp. 15-24 (published and (C) 1991 by the Faculty Press, Cambridge, Great Britain).

Mysliborski et al, "Therapy for Acne Vulgaris", *Comprehensive Therapy*, vol. 7, No. 1, pp. 13-16 (Jan. 1981).

Niemiec et al., "Influence of Nonionic Liposomal Composition on Topical Delivery of Peptide Drugs into Pilosebaceous Units: An in Vivo Study Using the Hamster Ear Model", Pharmaceutical Research, vol. 12, No. 8, 1995, pp. 1184-1188.

Odani et al., "Wheat Germ Trypsin Inhibitors. Isolation and Structural Characterization of Single-Headed and Double-Headed Inhibitors of the Bowman-Birk Type", *J. Biochem.*, vol. 100, pp. 975-983 (1986).

Official Compendia of Standards, USP 24 USP/NF 19-38 , US Pharmacopeial Convention, Inc. 2000 (Board of Trustees, US Pharmacopieal Convention, Inc.).

Ogawa, "Current Problem of Research on Hair Growth Mechanisms and Hair Growth Promoters", *Fragrance Journal*, vol. 5, pp. 1-5 (1989).

Orlow et al, "Subcellular Distribution Of Tyrosinase and Tyrosinase-Related Protein-1: Implications For Melanosomal Biogenesis", *The Journal of Investigative Dermatology, Inc.*, vol. 100, No. 1, Jan. 1993, pp. 55-64.

Quillien et al, "Trypsin Inhibitor Polymorphism: Multigene Family Expression and Posttranslational Modification", *Journal of Protein Chemistry*, vol. 16, No. 3 (1997) pp. 195-203.

Reiner, "Altered Cell Signaling and Mononuclear Phagocyte Deactivation During Interacellular Infection", *Immunology Today*, vol. 15, No. 8 (1994) pp. 374-381.

Ripka et al, "Chapter 8: Antithrombotics/Serine Protease", Covads International, San Diego, CA, publicly available prior to Feb. 28, 2001.

Robert et al, "Cell-Matrix Interactions In The Genesis Of Arteriosclerosis and Alateroma, Effect of Aging", *Laboratorie de Biologie du Tissu Conjonctif*, Annals New York Academy of Sciences, 1992, pp. 331-341.

Santulli et al, "Evidence for the Presence of a Protease-Activated Receptor Distinct from the Thrombin Receptor in Human Keratinocytes", *Proceeding of the National Academy of Sciences USA*, vol. 92, Sep. 1995, pp. 9151-9155.

Scotti, "Soy-derived Protease Inhibitors Treat Cancer and Inflammation", Windhover Information Inc. (1998).

Seiberg et al, "Trypsin-Induced Follicular Papilla Apoptosis Results in Delayed Hair Growth and Pigmentation", *Developmental Dynamics*, vol. 208, pp. 553-564 (1997).

Setchell, "High-Performance Liquid Chromatographic Analysis of Phytoestrogens in Soy Protein Preparations with Ultraviolet Electrochemical and Thermospray Mass Spectrometric Detection", *Journal of Chromotography*, vol. 386 (1987) pp. 315-323, CHROMSYMP. 956.

Sharpell et al, "Preservation of Cosmetics", Chapter 51, pp. 887-900, Disinfection, Sterilization and Preservation, 4th Edition, Seymour S. Block, Ph. D., Lea & Febiger (1991) publicly available prior to Feb. 28, 2001.

Sligh Jr. et al, "Inflammatory and Immune Responses are Imparied in Mice Deficient in Intercellular Adhesion Molecule 1", *Proc. Natl. Acad., Sci. USA*, vol. 90, 1993, pp. 8529-8533.

Song et al, "PS04.01.44 Crystal Structure of the Complex of Porcine Pancreatic Trypsin with Kunitz-Type Soybean Trypsin Inhibitor", Crystallography of Biological Macromolecules, p. C-106, XVII Congress and General Assembly of the International Union of Crystallog, (1996) (www.bmsc.wahing . . . ts/abstracts/S0081.html).

Song et al, "Kunitz-Type Soybean Trypsin Inhibitor Revisited: Refined Structure of its Complex with Porcine Trypsin Reveals and Insight into the Interaction Between a Homologous Inhibitor from Erythrina Caffra and Tissue-type Plasminogen Activator", *J. Mol. Biol.*, vol. 275, pp. 347-363 (1998).

Steenvoorden et al, "Protection Against UV-Induced Reactive Intermediate in Human Cells and Mouse Skin by Glutathione Precursos: A Comparison of N-Acetylcysteine and Glutathione Ethylester", *Photochemistry and Photobiology*, vol. 67, No. 6, pp. 651-656 (1998).

Steenvoorden et al, "The Use of Endogenous Antioxidants to Improve Photoprotection", *Journal of Photochemistry and Photobiology B: Biology*, vol. 41 (1997) pp. 1-10.

Stenn et al, "Glucocorticoid Effect on Hair Growth Initiation: A Reconsideration," *Skin Pharmacol.*, vol. 6, pp. 125-134 (1993).

Tan-Wilson, "Relevance of Multiple Soybean Trypsin Inhibitor Forms to Nutritional Quality", *Nutritional and Toxicological Significance of Enzyme Inhibitors in Foods*, Edited by Mendel Friedman, Chapter 22, pp. 391-411 (1985), Department of Biological Sciences, State University of New York at Binghamton.

Tashiro et al., "The Complete Amino Acid Sequence of Rice Bran Trypsin Inhibitor", *J. Biochem*, vol. 102, No. 2, pp. 297-306 (1987).

Terada et al, "Amino Acid Sequences of Double-headed Proteinase Inhibitors from the Seeds of Canavalia Lineata", *Biosci. Biotech. Biochem.*, vol. 58, No. 2, pp. 376-379 (1994).

Thornton et al, "Effect of Androgens on the Growth of Cultured Human Dermal Papilla Cells Derived from Beard and Scalp Hair Follicles", *The Journal of Investigative Dermatology*, vol. 97, No. 2, pp. 345-348 (Aug. 1991).

Travis et al, "The Role Of Proteolytic Enzymes In The Development Of Pumonary Emphysema And Periodontal Disease", *American Journal of Respiratory and Critical Care Medicine*, vol. 150,1994, pp. S143-S146.

Tronnier et al., "Adhesion Molecule Expression In Normal Skin and Melanocytic Lesions", *Journal of Cutaneous Pathology*, vol. 24, 1997, pp. 278-285.

Tyrrell et al., "Correlation Between Endogenous Glutathione Content and Sensitivity of Cultured Human Skin Cells to Radiation at Defined Wavelengths in the Solar Ultraviolet Range", *Photochemistry and Photobiology*, vol. 47, No. 3, pp. 405-412 (1988).

Van De Stolpe et al, "Intercellular Adhesion Molecule-1", *J. Mol. Med.*, vol. 74, 1996, pp. 13-33.

Van Den Broeke et al, "Topically Applied N-acetylcysteine as a Protector Against UVB-Induced Systemic ZImmunosuppression", *Journal of Photochemistry and Photobiology*, B: Biology, vol. 27, pp. 61-65 (1995).

Wang et al, "Effects of Soybean Trypsin Inhibitor on Digestive Physiology and Growth and Development of Helicoverpa Armigera Larvae", *Acta Entomologica Sinica*, vol. 38, No. 3 (Aug. 1995) pp. 272-274.

Webster, "Inflammation In Acne Vulgaris", *Journal of the American Academy of Dermatology*, vol. 33, No. 2, Part 1, 1995, pp. 247-253.

Wiley et al, "Cardiovascular and Renal—Small-molecule direct thrombin inhibitors", Exp. Opin. Ther. Patents, vol. 7, No. 11, 1997, pp. 1265-1282 (Ashley Publications Ltd. ISSN 1354-3776).

Xiang et al, "A Study of Nexin 1 of Skin and Hair Follicle during Postnatal Devleopment Period of Rat", Zhongguo Yi Xue Ke Xue Yaun Xue Bao, vol. 20, No. 2, pp. 127-132 (Apr. 1998) ABSTRACT.

Yu et al, "Message of Nexin 1, a Serine Protease Inhibitor, is Accumulated in the Follicular Papilla During Anagen of the Hair Cycle", Journal of Cell Science, vol. 108, Pt 12 (Dec. 1995) pp. 3867-3874 ABSTRACT.

Babiarz-Magee et al, "The Expression and Activation of Protease-Activated Receptor-2 Correlate with Skin Color", *Pigment Cell Res*, vol. 17 (2004) pp. 241-251.

Hermanns et al, "Unraveling the Patterns of Subclinical Pheomelanin-Enriched Facial Hyperpigmentation: Effect of Depigmenting Agents", *Dermatology*, vol. 201 (2000) pp. 118-122.

Liu et al, "Application of Soy in Skin Care", *Journal Nutr.*, vol. 132 (2002) pp. 574S.

Paine et al, "An Alternative Approach to Depigmentation by Soybean Extracts via Inhibition of the PAR-2 Pathway", *Journal Investigative Dermatology*, vol. 116 (2001) pp. 587-595.

Scott et al, "Protease-Activated Receptor 2, a Receptor Involved in Melanosome Transfer, is Upregulated in Human Skin by Ultraviolet Irradiation", *Journal Investigative Dermatology*, vol. 117 (2001) pp. 1412-1420.

Scott et al, "Proteinase-Activated Receptor-2 Stimulates Prostaglandin Production in Keratinocytes: Analysis of Prostaglandin Receptors on Human Melanocytes and Effects of PGE2 and PGF2α on Melanocyte Dendricity", *Journal Investigative Dermatology*, vol. 122 (2004) pp. 1214-1224.

Scott et al, "The Proteinase-Activated Receptor-2 Mediates Phagocytosis in a Pho-Dependent Manner in Human Keratinocytes", *Journal Investigative Dermatology*, vol. 121 (2003) pp. 529-541.

Seiberg et al, "Inhibition of Melanosome Transfer Results in Skin Lightening", *Journal Investigative Dermatology*, vol. 115 (2000) pp. 162-167.

Seiberg et al, "Soy Extracts Reduce Hair Growth and Hair Follicle Dimensions", *Hair Science and Technology*, D. Van Nesle (editor) (2003) pp. 391-400.

Seiberg et al, "Soymilk Reduces Hair Growth and Hair Follicle Dimensions", *Experimental Dermatology*, vol. 10 (2001) pp. 405-423.

Seiberg et al, "The Protease-Activated Receptor 2 Regulates Pigmentation via Keratinocyte-Melanocyte Interactions", *Experimental Cell Research*, vol. 254 (2000) pp. 25-32.

Seiberg et al, "The Protease-Activated Receptor-2 Regulates Pigmentation via melanosome Phagocytosis", *Mechanisms of Suntanning*, J. P. Ortonne and R. Ballotti (editors) (2002) pp. 215-278.

Seiberg et al, "The Regulation of Pigmentation by Serine Proteasses and Their Inhibitors", Inhibition of Human Proteases: From Target Identification to Therapy, CHI Press (1998) pp. 1-3.

Seiberg, "Keratinocyte-Melanocyte Interactions During Melanosome Transfer", *Pigment Cell Res.*, vol. 14 (2001) pp. 236-242.

Sharlow et al, "The Protease-Activated Receptor-2 Upregulates Keratinocyte Phagocytosis", *Journal of Cell Science*, vol. 113 (2000) pp. 3093-3101.

Wang et al, "Effects of Soybean Trypsin Inhibitor on Digestive Physiology and Growth and Development of Helicoverpa Armigera Larvae", *Acta Entomologica Sinica*, vol. 38, No. 3 (Aug. 1995) pp. 272-274.

Wilson et al, "Immunocytochemical Study of the Interaction of Soybean Trypsin Inhibitor with Rat Intestinal Mucosa", *Gut*, vol. 19 (1979) pp. 260-266.

Zajdela, F. et al., "Ultraviolet light induction of skin carcinoma in the mouse; influence of cAMP modifying agents"; Bull. Cancer, 65(3): 305-314 (1978).

Limtrakul, P. et al., "Suppressive Effect of Soybean Milk Protein on Experimentally Induced Skin Tumor in Mice"; Life Sciences, 53(21): 1591-1596 (1993).

Huang, M. et al., "Effects of Tea, Decaffeinated Tea, and Caffeine on UVB Light-induced Complete Carcinogenesis in SKH-1 Mice: Demonstration of Caffeine as a Biologically Important Constituent of Tea"; Cancer Research, 57: 2623-2629 (1997).

Lou, Y. et al., "Effects of Oral Administration of Tea, Decaffeinated Tea, and Caffeine on the Formation and Growth of Tumors in High-Risk SKH-1 Mice Previously Treated With Ultraviolet B Light"; Nutrition and Cancer, 33(2): 146-153 (1999).

NCBI PubMed; Clawson, G.A., "Protease inhibitors and carcinogenesis: a review."; Cancer Invest, 14(6): 597-608 (1996) [Abstract].

NCBI PubMed; YP, L. et al., "Stimulatory effect of oral administration of green tea or caffeine on ultraviolet light-induced increases in epidermal wild-type p53, p21(WAF1/CIP1), and apoptotic sunburn cells in SKH-1 mice."; Cancer Res., 60(17): 4785-91 (2000) [Abstract].

Official Action issued Dec. 26, 2003 for Chinese Application No. 00804580.1 in the National Phase of PCT/US98/09799.

Chen, H. et al. "Functions of Soybean Protein Products and Their Application in Cosmetics"; China Surfactant Detergent and Cosmetics (translated phonetically from the Chinese), 30(6): 62-64 (2000).

Printout from website: http://www/faqs.org/health/Sick-V1/Acne.html (7 sheets) (date shown on printed sheets: Oct. 31, 2006).

* cited by examiner

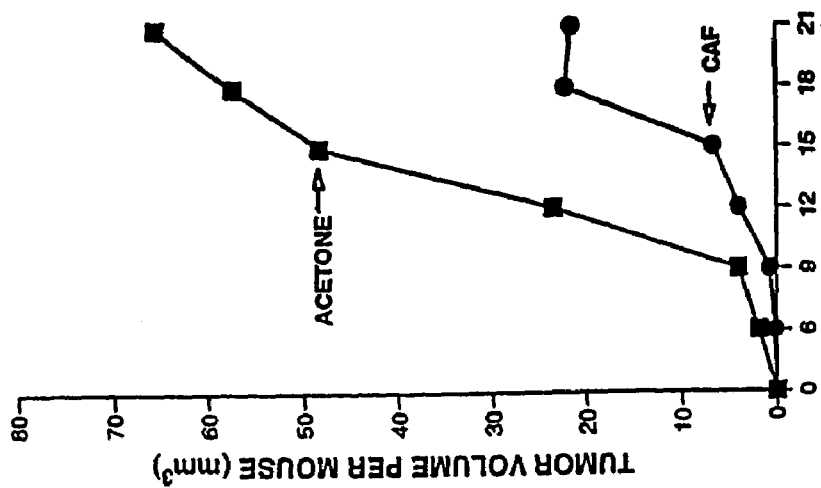
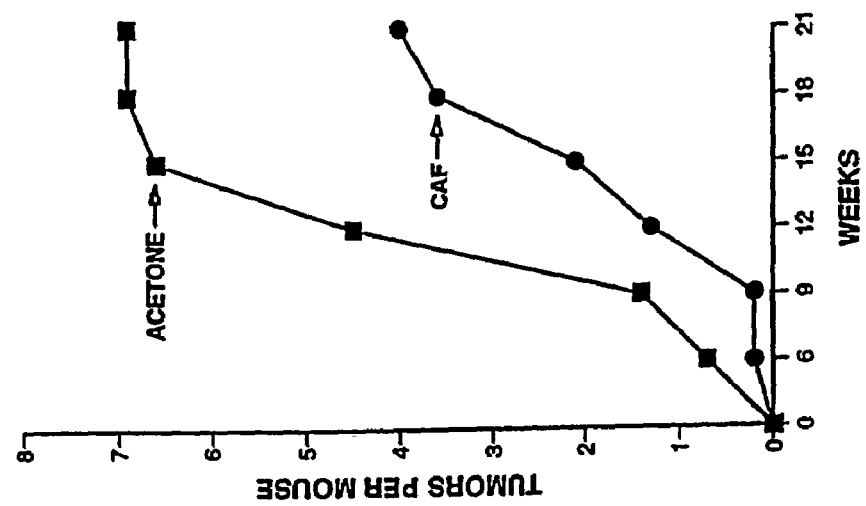
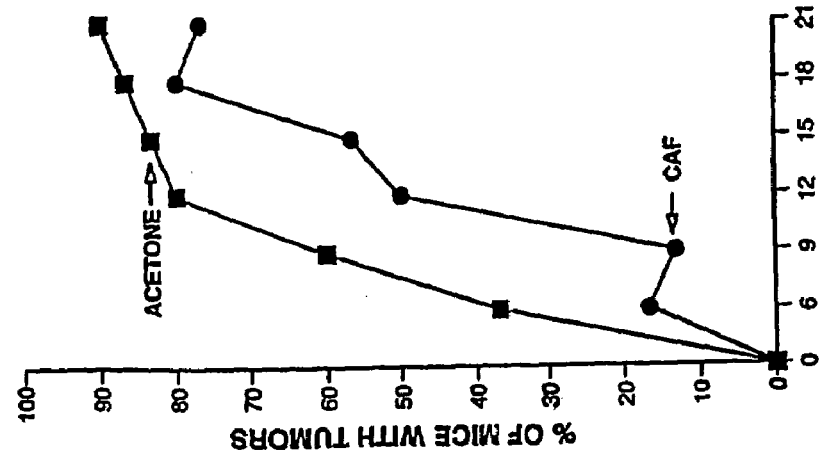
Fig. 3A
Fig. 3B
Fig. 3C

TOPICAL ANTI-CANCER COMPOSITIONS AND METHODS OF USE THEREOF

CROSS-REFERENCES TO RELATED APPLICATIONS

This application is a continuation in part of U.S. application Ser. No. 09/698,454 filed Oct. 27, 2000, the entire disclosure of which is incorporated by reference herein.

FIELD OF THE INVENTION

This invention relates to compositions containing non-denatured soy products, or soy trypsin inhibitors, and optionally additional anti-cancer or cosmetically active agents. These compositions can be applied topically to reduce the risk of UV-induced cutaneous tumors.

BACKGROUND OF THE INVENTION

Skin, the largest organ of the human body, is continuously exposed to environmental insults such as smoke, pollution, and ultraviolet (UV) irradiation. The thinning of the ozone layer, which is expected to progress for at least several decades, reduces a major barrier to the passage of ultraviolet-B radiation (UVB) through the atmosphere. UVB, that is, light whose wavelength is in the range between about 280 and about 320 nm, is the main cause of sunburn, tanning, aging of the skin, and skin cancer.

The non-melanoma skin cancers (NMSC), including basal-cell and squamous-cell carcinoma, are the most common types of cancer among Caucasian populations. The incidence of NMSC has increased worldwide over the last few decades. Increased recreational and occupational sunlight exposure is commonly regarded as one of the reasons for the higher incidence of cutaneous cancers. The increase in UVB exposure associated with the thinning of the ozone layer is another significant factor. Mortality from NMSC is low, but the estimated recurrence rate of about 50% after five years and the local invasiveness of this type of cancer result in high medical costs. Therefore, NMSC constitutes a substantial public health concern. (Reviewed in Holick and Kligman, editors: Biologic effects of light. Walter de Gruyter, Berlin and New York, 1992).

Photo-carcinogenesis results from a complex interplay of simultaneous and sequential biochemical events. These events, initiated by irradiation of an organism with UV light of an appropriate wavelength, include the formation of DNA photo-products, inaccuracies in DNA repair, mutation of proto-oncogenes and tumor suppressor genes, and UV-induced production of radical species which produce subsequent effects on existing mutations and independently induce further mutations. In addition, other epigenetic events such as immunological responses, antioxidant defenses, and dietary factors may influence the course of carcinogenesis. (Black, H. S., deGruijl, F. R., Forbes P. D., Cleaver, J. E., Ananthaswamy, H. N., deFabo, E. C., Ullrich, S. E., Tyrrell, R. M., Photo-carcinogensis: an overview. J. Photochem. Photobiol. B 40:1, 29-47, Aug., 1997).

The skin possesses an elaborate antioxidant defense system to deal with UV-induced oxidative stress. Excessive exposure to UV radiation, however, can overwhelm the cutaneous antioxidant capacity, leading to oxidative damage and ultimately to skin cancer and premature skin aging. Therefore, one strategy for photo-protection is to support the endogenous antioxidant system by induction or transdermal delivery of antioxidant enzymes or nonenzymatic antioxidants. Antioxidants such as glutathione, alpha-tocopherol, ascorbate and beta-carotene have been found to be very effective in photoprotection. Components of the antioxidant pathway have also been identified and applied to the skin of patients. Although skin treatments with single components of the antioxidant system such as vitamin E were successful against a wide variety of types of photodamage, they were not shown to affect the progression of UV-induced tumors. The most promising results were obtained in studies combining several compounds, which often resulted in synergy between the protective effects. (Steenvoorden D. D., van Henegouwen G. M., The use of endogenous antioxidants to improve photoprotection, J. Photochem. Photobiol., B 41:1-2, 1-10, November, 1997).

Epidemiological studies suggest that components of vegetables, particularly legumes, are beneficial in lowering the incidence rates of many types of cancer. For example, the rates of breast, colon and prostate cancer are significantly lower among the inhabitants of most countries of the Pacific Basin, but offspring of Pacific Basin natives who have migrated to the United States develop the common Western cancers at approximately the same rate as native Westerners. Such epidemiological studies suggest that dietary and other environmental factors, rather than genetic differences, contribute more significantly to the risk of susceptibility to these cancers. The high consumption of soybean products in Pacific Basin countries, such as Japan, implicates diet as one factor contributing to the relatively extremely low rates of cancer mortality in these countries. (E.g., Wu et al., Soy intake and risk of breast cancer in Asians and Asian Americans. Am. J. Clin. Nutr. 68: 6 Suppl., 1437S-1443S, December, 1998).

Soybeans are a rich source of isoflavones, which possess weak estrogenic activity. Genistein, the main soybean isoflavone, is a specific inhibitor of protein tyrosine kinases and of other enzymes involved in signal transduction. Genistein has been shown to suppress the growth of numerous cancer cells in vitro, and to protect animals in experimental carcinogenesis models from developing both hormone- and non-hormone related cancers. (Reviewed in A. R. Kennedy, Chemopreventive agents: Protease inhibitors, Pharmacology Theories 78 (3), 167-209), 1998 and in Messina et al., Soy intake and cancer risks: A review of the in vitro and in vivo data, Nutrition and Cancer 21 (2), 113-131, 1994).

Soybeans also contain a number of protease inhibitors such as BBI and STI. It is important to note that soy foods do not contain high concentrations of active STI and BBI, because these protease inhibitors block the action of trypsin and other enzymes needed for protein digestion. Although STI is denatured by cooking, heat alone does not inactivate BBI, and consumption of soy products containing high levels of these protease inhibitors leads to serious digestive problems, chronic deficiency in amino acid uptake, and cancer. Indeed, the Chinese did not serve soybeans as food until fermentation techniques were developed to destroy the anti-digestive properties of the soy foods (2nd century B.C.E.). During the production of soy foods today, pureed soybeans are soaked in an alkaline solution and then pressure-heated to 115° C. in order to denature the protease inhibitors as much as possible.

Limtrakul et al. attempted to identify a safe level of soy proteins for nutritional consumption, which would be beneficial in the prevention of cancer. Skin tumors were chemically induced in mice, which were fed soy protein isolate (SPI) exclusively, and in mice which were fed SPI supplemented with soymilk proteins (SMP). It was reported that "the percentage of tumor-bearing mice and the volume of tumor tended to be lower in the mice on the SMP diet". *Life Sciences* 1993, 53, 1591-1596. When defatted soybeans are treated first with alkaline, then with acid solution, SPI is the precipitate and SMP is the supernatant. The Limtrakul study shows the potential of soy proteins to affect skin cancer progression, when the proteins are orally consumed. However, it was also emphasized that higher levels of dietary intake of SMP would result in major health problems.

It is clear that a need exists for safe, efficacious and economical agents that prevent or reduce incidence of cancer, particularly for NMSC, which may be simply and conveniently administered. Further, economical and prophylactic compositions and methods for the reduction, prevention or inhibition of the progression of UV-induced cutaneous tumors are highly desirable. Since topical application is very simple and convenient, incorporating compositions that reduce skin cancer incidence into a skin-care product would be extremely advantageous. While sunscreens are known to reduce the damage resulting from UV exposure during the period of their application, there is a need for a skin care product that could also slow the progression of already-initiated photocarcinogenic processes. It is an object of the invention to provide such a product.

SUMMARY OF THE INVENTION

The present invention provides a method of reducing the risk of developing UV-induced tumors of the skin of a mammal by topically applying a skin-care composition, preferably to an individual who has already been exposed to or irradiated with UV light. A method of reducing the growth rate of UV-induced cutaneous tumors by topically applying the skin-care composition is also provided, as is a method of preventing the progression of cancer by the same means.

The skin care composition for use in the methods of the invention is formulated for the topical delivery of a non-denatured soy product (e.g., to a mammal such as a human) and comprises a soy product (e.g., a non-denatured soymilk or soybean powder or soybean trypsin inhibitor) and a vehicle. The composition may optionally comprise other anti-cancer or cosmetically active agents. Certain skin care compositions appropriate for use in the present invention have been described in U.S. patent application Ser. Nos. 09/110,409, 09/621,565 and 09/698,454, filed Jul. 6, 1998, Jul. 21, 2000 and Oct. 27, 2000, respectively, and in International Application No. WO99/04752. Each of the foregoing patent documents is incorporated herein by reference.

Other features and advantages of the present invention will be apparent to those of skill in the art in light of the following description and claims.

BRIEF DESCRIPTION OF THE DRAWINGS

FIGS. 3A-3C are a series of graphs showing the inhibitory effects caffeine on the development of skin tumors in SKH-1 mice previously treated with ultraviolet B light.

DETAILED DESCRIPTION OF THE PREFERRED EMBODIMENTS

Figure 1C:
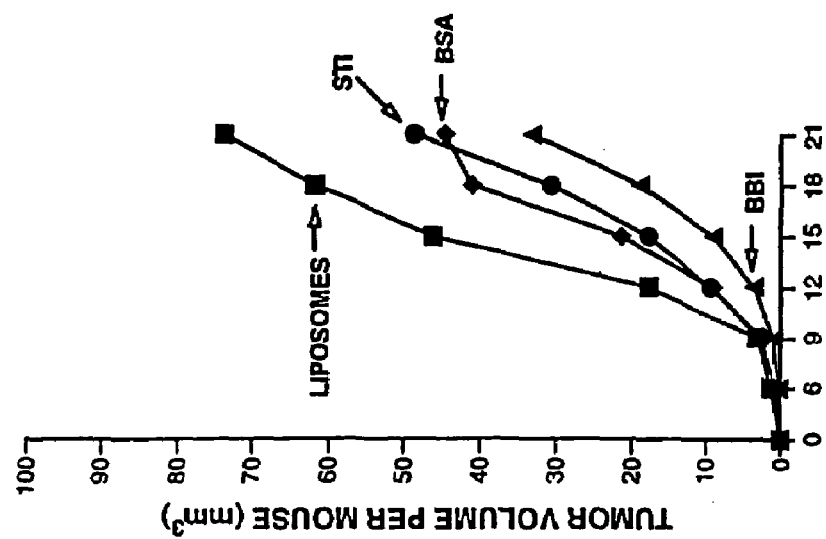
FIGS. 1A-1C are a series of graphs showing the inhibitory effects of STI and BBI on the development of skin tumors in SKH-1 mice previously treated with ultraviolet B light. (BSA—bovine serum albumin; BBI—Bowman-Birk Inhibitor; STI—Soy Bean Trypsin Inhibitor)
Figure 1B:
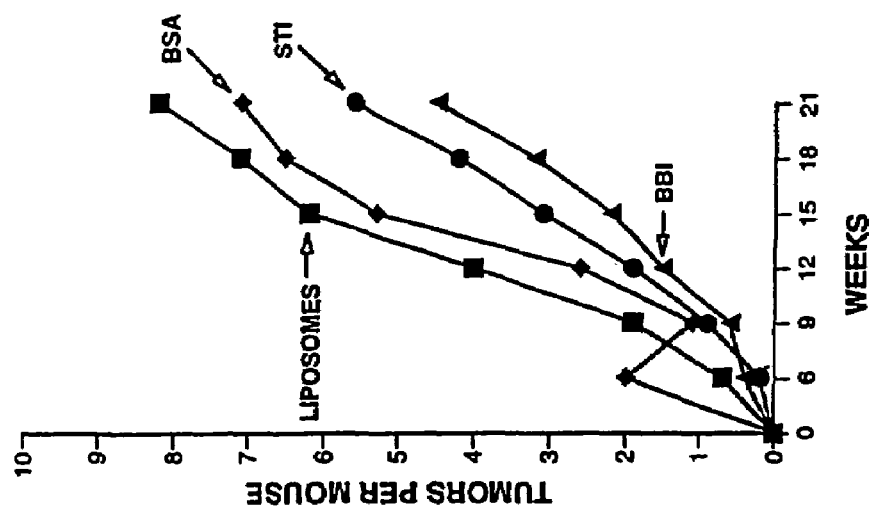
Figure 1A:
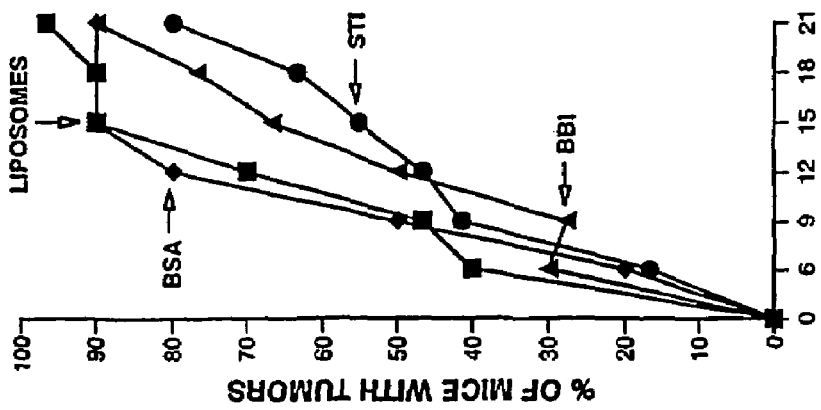

It is believed that one skilled in the art can, based upon the description herein, utilize the present invention to its fullest extent. The following specific embodiments are to be construed as merely illustrative and not limitative of the remainder of the disclosure. All publications, patent applications, patents, and other references mentioned herein are incorporated by reference in their entirety.

The present invention is directed to soy-containing compositions and methods of use thereof in the prevention and reduction of the risk of skin cancer. The novel compositions of this invention contain legume products, and preferably soy products, that may be in the form of a fluid (e.g., soymilk) or a solid (e.g., a soybean powder or soymilk powder). What is meant by "soy product" is a substance derived from the soybean, containing the ingredients naturally found in soybeans, at the relative concentrations as found in the beans, excluding water content. In one embodiment, the soy product is a non denatured soy product.

"Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)".

What is meant by "non-denatured soy product" is a soy product in which the processing for the derivation of such soy product (e.g., the temperature, extraction media) did not eliminate its protease inhibitory activity. In one embodiment, the non-denatured state of the soy product of this invention is measured by the presence of an intact soybean trypsin inhibitor (STI) protein.

In another embodiment, the soy product is soymilk. One way to make soymilk is to soak the soybeans in deionized or purified water for several hours, and grind them after they were fully hydrated, with the addition of small quantities of water. (The grinding process allows the soybean milk to be extracted). After collection, the soybean milk may be filtered to remove any residual parts of the bean husk. The soymilk used in this invention can be fresh soymilk as described above, or may be made from soybean powder and water. The soybean powder is milled from soybeans and may also be lyophilized, spray dried, or freeze-dried and the resulting soymilk may or may not be filtered. Soymilk prepared by these methods may have from about 1 to about 90% by weight dry soybean powder. Another example is the use of soymilk powder, made from lyophilized, spray dried or freeze-dried soymilk, with the addition of water and finished with or without filtration or homogenization.

Other methods of soybean extraction could also be used to create the active ingredients used in this invention. In one example, the active ingredients could be extracted from ground soybeans using ethanol/water mixtures, followed by the removal of the ethanol from the extract, in such ways that the protease inhibitory activity of the soybean will be retained.

The compositions of the present invention may contain from about 1% to about 99%, by weight, of the soy product. For example, when a liquid soy product (e.g., soymilk) is used, the composition may contain from about 50% to about 99%, by weight, (e.g., from about 70% to about 99%) of the liquid soy product. For example, when a solid soy product (e.g., soybean powder or soymilk powder) is used, the composition may contain from about 1% to about 50%, by weight (e.g., from about 2% to about 30%, by weight) of the solid soy product. Compositions comprising solid soy products may also comprise water (e.g., distilled water or water contained within soymilk) to form a liquid base for the composition (e.g., to form a cream, lotion, injectable solution or gel). Such compositions may comprise from about 50% to about 98%, by weight (e.g., from about 70% to about 98%, by weight) of water. While not limited to these methods of administration, the compositions of this invention may be delivered topically, orally, or parenterally, although topical administration is preferred.

The soy products useful in this invention may be produced from all soybean species, regardless of their geographic origin, sun exposure, harvest time and the like. However, specific strains, geographic origins or growth conditions might be preferred. These include soybean strains or other legume strains particularly rich in their trypsin inhibitor (e.g. STI, LTI, BBI) content or strains in which, under the proper growth conditions trypsin inhibitor enrichment occurs in the bean. It should be noted that the legume products useful in the compositions of this invention have a distinctive odor, which may be tolerable in some cultures, but is undesired in others. If necessary, the odor of the compositions of this invention can be reduced by using soybean products derived from specific strains of soybeans known to be less odiferous, including, but not limited to, lipoxygenase-2-deficient beans and those having a modified sugar profile, or the like. A process to reduce oxygen levels in the formulation may also reduce the odor. Various masking agents or fragrances may also be used to mask the odor.

In yet another embodiment of the invention, the soy-containing compositions may optionally comprise additional synthetic or natural anti-cancer agents. Examples of such agents include, without limitation, caffeine, Milk Thistle extract, green tea extract, epigallocathechin gallate, silymarins, glucocorticoids and 5-fluorouracil.

A preferred embodiment of the invention comprises the administration of soymilk containing compositions before or after the initiation of UV-induced skin cancer. Especially preferred are embodiments in which the soymilk is not denatured, leaving STI and BBI intact. Soymilk also contains genistein and other isoflavones, and anti-oxidants such as the gamma form of vitamin E, which is essential to the health of the skin. While not wishing to be held to any particular theory, it is hypothesized that these different active components also participate in the prevention of tumor progression. Soymilk also contains lecithins and other emulsifying molecules that facilitate the transdermal delivery of the active components.

As explained above, the present invention extends to a topical cosmetic or pharmaceutical composition comprising a non-denatured soy product (e.g., a non-denatured soymilk or soybean powder) and a cosmetic or pharmaceutically acceptable vehicle and, optionally, additional anti-cancer or cosmetically active agents. As used herein, "topically applying" means directly laying on or spreading on outer skin, e.g., by use of the hands or an applicator such as a wipe, roller, or spray.

The phrase "cosmetic or pharmaceutically acceptable" refers to entities and compositions that are physiologically tolerable and do not typically produce an allergic or similar untoward reaction when administered to a human. As used herein, "cosmetically acceptable" means that the ingredients which the term describes are suitable for use in contact with tissues (e.g., the skin) without undue toxicity, incompatibility, instability, irritation, allergic response, and the like.

The term "vehicle" refers to a diluent, adjuvant, excipient, or carrier. Such cosmetic or pharmaceutical vehicles can be liquids, such as water and oils, including those of petroleum, animal, vegetable or synthetic origin, such as peanut oil, soybean oil, mineral oil, sesame oil and the like. In the art of formulating skin care compositions, the vehicle is often an oil-in-water or a water-in-oil emulsion. Suitable pharmaceutical carriers are described in "Remington's Pharmaceutical Sciences" by E. W. Martin. Suitable cosmetic carriers are described below.

The compositions for use in the methods of the present invention include formulations suitable for topical application to skin. In one embodiment, the composition comprises a non-denatured soy product and a cosmetically acceptable topical carrier. In one embodiment, the cosmetically acceptable topical carrier is from about 50% to about 99.99%, by weight, of the composition (e.g., from about 80% to about 99%, by weight, of the composition).

The compositions may be made into a wide variety of product types that include, but are not limited to, solutions, lotions, creams, gels, sticks, sprays, ointments, cleansing liquid washes, solid bars, shampoos, pastes, foams, powders, mousses, shaving creams, wipes, patches, nail lacquers, wound dressing, adhesive bandages, hydrogels, and films. Make-up, such as foundations, mascaras, and lipsticks also form suitable compositions. These product types may comprise several types of cosmetically acceptable topical carriers including, but not limited to solutions, emulsions (e.g., microemulsions and nanoemulsions), gels, solids and liposomes. Certain non-limitative examples of such carriers are set forth hereinbelow. Other suitable carriers may be formulated by those of ordinary skill in the art.

Topical compositions useful in the subject invention may be formulated as a solution comprising an emollient. Such compositions preferably contain from about 1% to about 50% of an emollient(s). As used herein, the term "emollient" refers to materials used for the prevention or relief of dryness, as well as for the protection of the skin. A wide variety of suitable emollients is known and may be used in the present invention. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7$^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present invention may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp.1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well known in the cosmetic art and are useful in the present invention. Multiphase emulsion compositions, for example the water-in-oil-in-water type, as disclosed in U.S. Pat. Nos. 4,254,105 and 4,960,764, may also be useful in the present invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

The topical compositions of the present invention can also be formulated as a solid formulation (e.g., a wax-based stick, soap bar composition, powder, or a wipe containing powder).

Liposomal formulations are also useful compositions of the subject invention. In one embodiment, the soymilk or soybean powder particles or soy proteins such as STI are contained within the liposome. Examples of liposomes are unilamellar, multilamellar, and paucilamellar liposomes, which may or may not contain phospholipids. Such compositions can be prepared by first combining the non-denatured soy milk product or the STI with a phospholipid, such as dipalmitoylphosphatidyl choline, cholesterol and water. An example of a method for producing liposomes is described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473-474. Those of skill in the art may make suitable modifications of the method described therein.

Epidermal lipids of suitable composition for forming liposomes may be substituted for the phospholipid. The liposome preparation may then be incorporated into one of the above carriers (e.g., a gel or an oil-in-water emulsion) in order to produce the liposomal formulation. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345-358, PCT Patent Application No. WO96/31194, Niemiec, et al., 12 Pharm. Res. 1184-88 (1995), and U.S. Pat. No. 5,260,065.

In one embodiment, the liposome is nonionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome comprises glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 5 mg/ml to about 100 mg/ml such as from about 10 mg/ml to about 50 mg/ml.

The topical compositions useful in the subject invention may contain, in addition to the aforementioned components, a wide variety of additional oil-soluble materials and/or water-soluble materials conventionally used in compositions for use on skin, hair, and nails at their art-established levels.

In addition to such agents, other emollients and surface active agents can be incorporated in the emulsions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

The pharmaceutical or cosmetic composition may be optionally combined with other ingredients such as moisturizers, cosmetic adjuvants, anti-oxidants, depigmenting agents, darkening agents, anti-aging agents, hair removal agents, hair styling agents, nail styling agents, sunscreens, surfactants, bleaching agents, foaming agents, conditioners, humectants, fragrances, colorants, viscosifiers, buffering agents, preservatives, and the like and mixtures thereof. Skin-care compositions including these components should be formulated so as not to affect the soy product or soy trypsin inhibitory activity.

Examples of humectants include glycerol, sorbitol, propylene glycol, ethylene glycol, 1,3-butylene glycol, polypropylene glycol, xylitol, malitol, lactitol, allantoin, acetamine MEA, oat protein, hyaluronic acid, and the like. They may be used either singly or in combination.

Because the compositions of this invention are non-denatured, i.e., compositions in which the protease inhibitory activity is retained, they may be more favorable as a medium for microbial growth. Preservatives are useful for substantially preventing microbial decomposition. Examples of preservatives include phenoxyethanol and parabens such as methyl-paraben, ethyl-paraben, and propyl-paraben; salicylic acid, chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate, isothiazolones and the like. Other examples of preservatives are listed on pages 1654-55 of the International Cosmetic Ingredient Dictionary and Handbook, eds. Wenninger and McEwen (CTFA, $7^{th}$ ed., 1997), hereinafter referred to as the "Cosmetic Handbook." The composition may comprise from about 0.01% to about 20%, by weight (more preferably, from about 0.5% to about 5%, by weight) of preservative. Microbial contamination can also be eliminated by gamma irradiation or microfiltration, or by brief heat treatments that do not result in the elimination of protease inhibitory activity.

Examples of fragrances and odor masks include menthol, anethole, carvone, eugenol, limonene, ocimene, n-decylalcohol, citronellol, a-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, eucalyptus oil and the like.

Examples of surface active agents include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium α-olefin sulfonate and sodium dioctylsulfosuccinate; N-alkylaminoglycerols, e.g., N-lauryldiaminoethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic™ type surface active agent, and polyoxyethylenesorbitan aliphatic acid esters such as polyoxyethylenesorbitan monooleate and polyoxyethylenesorbitan monolaurate.

Examples of the binder or thickener include cellulose derivatives such as alkali metal salts of carboxymethylcellulose, methyl cellulose, hydroxyethyl cellulose and sodium carboxymethylhydroxyethyl cellulose, alkali metal alginates such as sodium alginate, propylene glycol alginate, gums such as carrageenan, xanthan gum, tragacanth gum, caraya gum and gum arabic, and synthetic binders such as polyvinyl alcohol, polysodium acrylate and polyvinyl pyrrolidone. Thickening agents that can be added to the compositions of this invention to alter viscosity include other polymers such as polyacrylates (e.g., polyacrylamide). Other examples of viscosity modifying agents are listed on pages 1692-97 of the Cosmetic Handbook. To achieve the appropriate viscosity, compositions of the present invention may comprise from about 0.01% to about 20%, by weight (e.g., from about 0.1% to about 5%, by weight) of a thickening agent.

Coloring agents and fragrances also are commonly included in such compositions.

In one embodiment, the topical composition further comprises another cosmetically active agent in addition to the non-denatured soy product. A "cosmetically active agent" is a compound (e.g., a synthetic compound or a compound isolated from a natural source or a natural extract) that has a cosmetic or therapeutic effect on the skin, hair, or nails, including, but not limiting to, lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

The compositions of this invention may be applied prior to, concurrently with or after other active ingredients or compositions to enhance their effect.

Antioxidants and/or chelating agents may also be used to increase shelf life and stability of the compositions. Antioxidants may be added both for formulation stabilization and for biological efficacy. Antioxidant compounds and their derivatives include, but are not limited to, water-soluble antioxidants such as sulfhydryl compounds and their derivatives (e.g., sodium metabisulfite and N-acetyl-cysteine), lipoic acid and dihydrolipoic acid, resveratrol, acetyl-cysteine (Iniferine®) or lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis, and legume extracts. Other examples of antioxidants may be found on pages 1612-13 of the Cosmetic Handbook. The compositions of the present invention may comprises the antioxidant in an amount of from about 0.001% to about 20%, by weight (e.g., from about 0.01% to about 10% by weight) of the composition.

It is preferable to have at least one oil-soluble antioxidant in the compositions of this invention. The antioxidants should be utilized in a stabilizing effective amount and may range in total from about 0.001 to 10% based on the weight of the total composition, preferably from about 0.005 to about 5%. The oil-soluble antioxidants which are useful in the compositions of the present invention include butylated hydroxytoluene (BHT), ascorbyl palmitate, butylated hydroxanisole (BHA), phenyl-α-naphthylamine, hydroquinone, propyl gallate, nordihydroguiaretic acid, and mixtures thereof as well as any other known oil-soluble antioxidant compatible with the other components of the compositions.

Preferably, a water-soluble antioxidant should also be present in the water phase of the compositions of this invention. The water-soluble antioxidants which are useful in the compositions of this invention include ascorbic acid, sodium metabisulfite, sodium bisulfite, sodium thiosulfite, sodium formaldehyde sulfoxylate, isoascorbic acid, thioglyerol, thiosorbitol, thiourea, thioglycolic acid, cysteine hydrochloride, 1,4-diazobicyclo-(2,2,2)-octane and mixtures thereof as well as any other known water-soluble antioxidant compatible with the other components of the compositions.

Chelating agents are also useful in assisting the stabilization of the compositions of this invention. Examples of chelating agents include EDTA and derivatives thereof (e.g., disodium EDTA and dipotassium EDTA), Iniferine ®, lactoferrin, and citric acid. Other examples of chelating agents are listed on page 1626 of the Cosmetic Handbook. The compositions of the present invention may comprise the chelating agent in an amount of from about 0.001% to about 20%, by weight (e.g., from about 0.01% to about 10% by weight) of the composition.

Other active ingredients such as sunscreen materials may be utilized in the compositions of the present invention provided that they are physically and chemically compatible with the other components of the compositions. Sunscreens may include organic or inorganic sunscreens, such as methoxyoctylcinnamate and other cinnamate compounds, titanium dioxide and zinc oxide and the like.

Various irritancy mitigants may be added to the compositions of this invention. Irritancy mitigants such as α-bisabolol, panthenol, allantoin, ginkgo biloba, stearoyl glycerrhetinic acid (licorice extract), tea tree oil, butchers' broom, calendula, ginseng and the like may be added.

Other ingredients may include agents that assist in protecting the skin from aging, such as sunscreens, anti-oxidant vitamins such as ascorbic acid, vitamin B, biotin, pantothenic acid, vitamin D, vitamin E and vitamin C, and sodium bisulfite. Yeast extract, ginkgo biloba, bisabolol, panthenol, alpha hydroxy acids and oligosaccharides such as melibiose are among other ingredients which assist in preventing aging of the skin by such means as irritation mitigation, oxidation mitigation, healing, affecting retinoid metabolism and inhibiting the production of elastase.

The compositions of this invention may also contain other depigmenting agents in addition to the soy product. What is meant by depigmentation is the lightening of the color of an area of skin, including but not limited to, the global lightening of the user's skin tone/complexion (e.g., the face, hands, or whole body, which is uneven as a result of aging skin, or darker than desired because of ethnicity or pathology, and the like), the evening of skin color tone, or the specific lightening of age spots, freckles, or darker pigmented areas such as, but not limited to, post-inflammatory hyper-pigmentary lesions.

Examples of such depigmenting agents include, but are not limited to, lipoic acid, dihydrolipoic acid, resveratrol, ascorbic acid, kojic acid, hydroquinone, isoflavones, retinoids (e.g., retinol, retinoic acid, and retinyl palmitate), tyrosinase inhibitors, melanosome transfer inhibitors, and selective cytotoxic agents for melanocytes, or natural extracts, e.g., licorice extract, gatuline A (pilewort extract), and micromerol (butylene glycol and apple extract), providing these activities. The amount of the depigmenting agent used will depend on the activity of the compound, and will typically range from about 0.001% to about 20%, by weight (e.g., from about 0.01% to about 10%, by weight) of the composition.

Other skin color evening ingredients, such as skin darkening or sunless tanning agents, may also be effective in the skin care compositions for use in this invention.

The composition of the present invention may also contain compounds that enhance the feel of the composition on the skin of the user. Examples of such compounds include, but are not limited to, oils, silicones (e.g., siloxane polymers such as dimethicone) and skin-conditioning agents such as emollients, and humectants. Examples of such skin conditioning agents may be found of pages 1656-1670 of the Cosmetic Handbook.

Compositions which assist in the reduction of lines and wrinkles may also be added to the compositions of this invention. For example, alpha hydroxy acids, hyaluronic acid, Gatuline R (fagus silvitica extract), pigments and scattering aids such as zinc oxide and titanium dioxide may be used in the compositions of this invention in this capacity.

Anti-inflammatory agents may also be used in the compositions of this invention. Not only should these agents assist in mitigating irritation, they may assist in treating wrinkles and lines in the skin. Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone and mixtures thereof may be used. Preferably, hydrocortisone or natural extracts with similar activity may be used.

Nonsteroidal anti-inflammatory agents may also be employed in the compositions of this invention, such as salicylates, acetic acid derivatives, fenamates, propionic acid derivatives and pyrazoles or mixtures thereof. Other synthetic and natural anti-inflammatory agents may also be used.

Additional active ingredients having topical activity may be utilized in the compositions of this invention. Azole-type anti-fungal and anti-bacterial agents may be employed in the compositions of this invention in their base form. For example, ketoconazole, miconazole, itraconazole, elubiol, and like related imidazole antifungals and antibacterials are useful in the topical formulations of this invention.

It can be readily appreciated that a transdermal route of administration may be enhanced by use of a dermal penetration enhancer, e.g., such as enhancers described in U.S. Pat. No. 5,164,189, U.S. Pat. No. 5,008,110, and U.S. Pat. No. 4,879,119, issued Nov. 7, 1989 to Aruga et al. In one embodiment, a composition of the present invention can be delivered in a controlled release system, such as using a transdermal patch, liposomes, or other modes of administration. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)].

In another embodiment, a controlled release system can be placed in proximity of the target tissues of the mammal, thus requiring only a fraction of the systemic dose [see, e.g., Goodson, in Medical Applications of Controlled Release, supra, vol. 2, pp. 115-138 (1984)]. In particular, a controlled release system can be introduced into an animal in proximity of the site of inappropriate immune activation or a tumor. Other controlled release systems are discussed in a review by Langer [Science 249:1527-1533 (1990)].

Figure 2C:
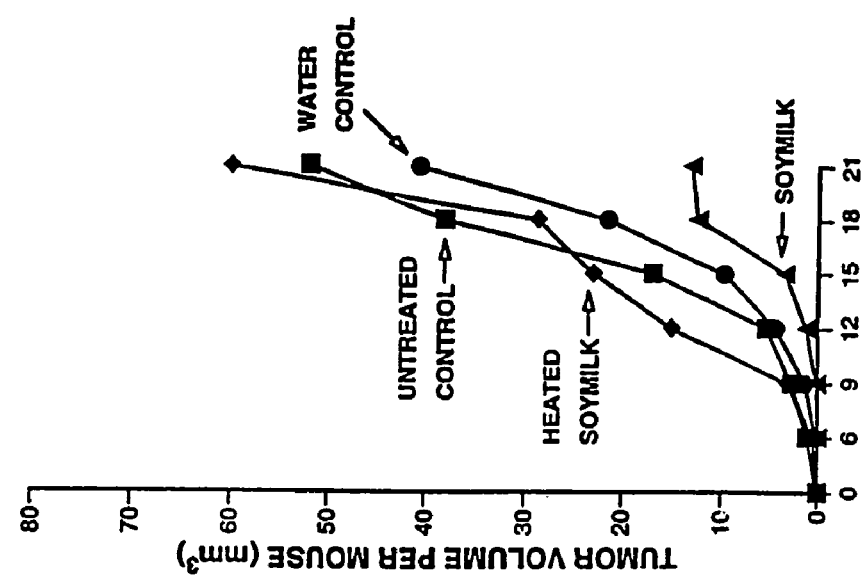
FIGS. 2A-2C are a series of graphs showing the inhibitory effect of Soymilk on the development of skin tumors in SKH-1 mice previously treated with ultraviolet B light. The inhibitory effects of heat-denatured soymilk vs. non-denatured soymilk are compared.
Figure 2B:
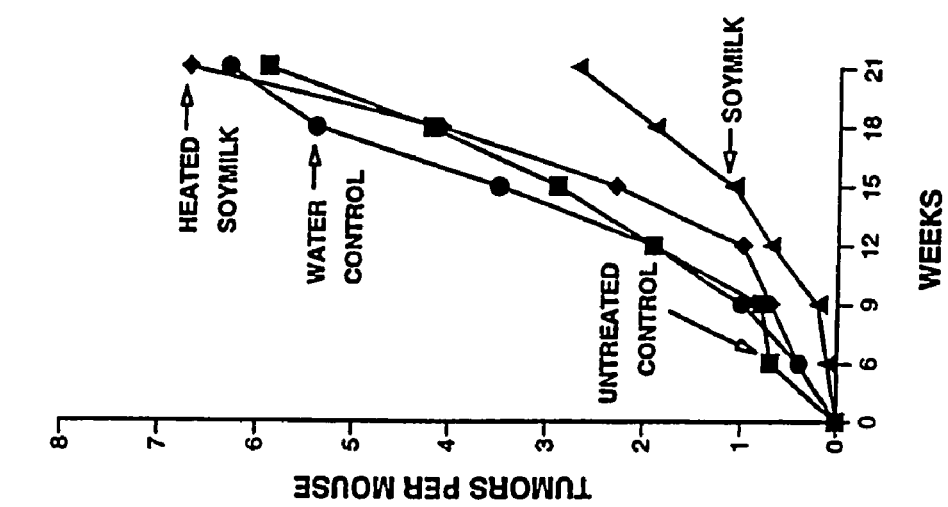
Figure 2A:
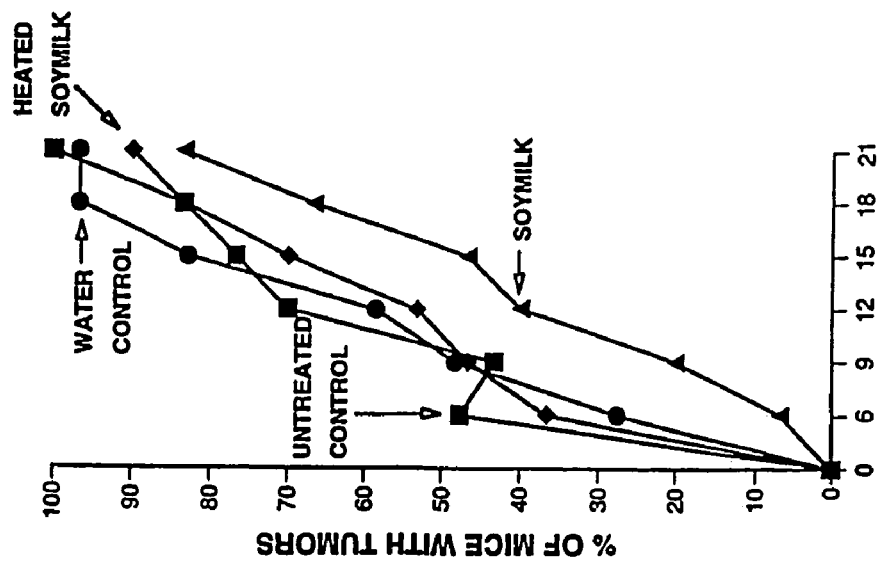
Figure 4A:
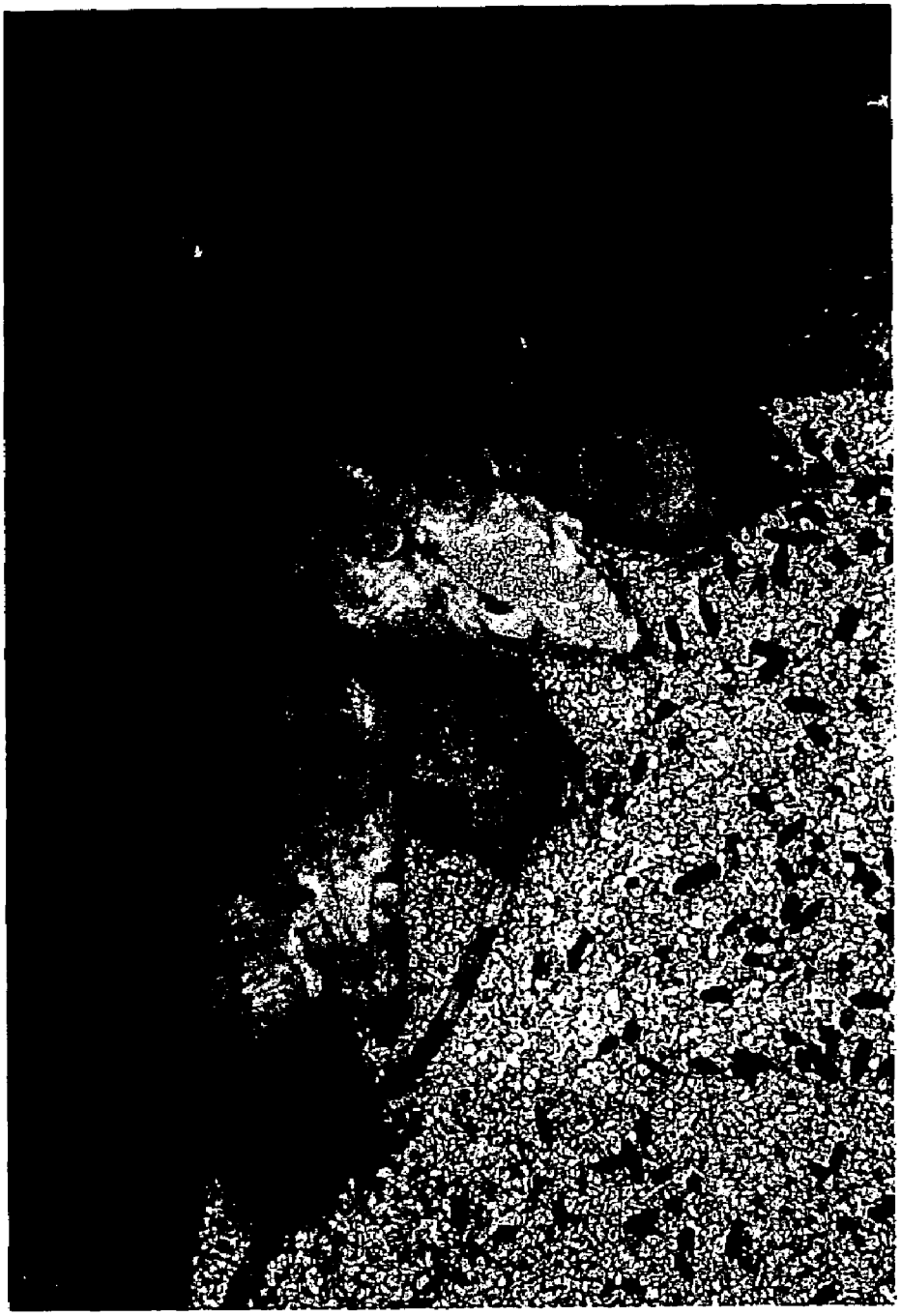
FIGS. 4A-4C are three photographs showing the reduction in size and number of UV-induced tumors among mice treated topically with non-denatured soymilk (FIG. 4A) compared to mice treated with heat-denatured soymilk (FIG. 4B) or water (FIG. 4C).
Figure 4B:
Figure 4C:

In yet another embodiment of the invention, the soybean trypsin inhibitor may be produced by recombinant means. The nucleotide and protein sequences of STI are known. See GenBank Accession No. AF314823. Methods for recombinant expression of STI are well known to those of ordinary skill in the art. In an alternative embodiment, the STI so produced may be modified at the genetic level (e.g. replacing amino acids to change local charges, to enhance skin penetration without compromising activity, or to enhance activity without compromising skin penetration) or chemically post synthesis (e.g. additional lipid or sugar groups) to enhance uptake of the STI into the skin of the patient.

Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis.

Compositions of the present invention may be prepared by mixing the desired ingredients. For example, soymilk is mixed with the chelating agent, preservative, and/or antioxidant. A thickener is then added to the system, and the mixture is further mixed until it reaches homogeneity at the desired viscosity. The compositions of the present invention may be prepared under an argon, nitrogen, or other inert gaseous blanket in order to enhance formulation stability and/or to reduce soybean odor. The compositions of this invention may be packaged in a tube, a sealed packet, a jar, a pump, a bottle, a can, a pledget, a towelet, a wipe or the like. An airtight package such as an aluminum tube, aluminum pocket, pump, laminate tube, or the like, can also be used to further enhance product stability.

The skin-care compositions for use in the methods of this invention may be applied daily for at least four weeks, and more preferably at least eight weeks, by which an effect upon the appearance of skin should be observed. Application may be continued as long as desired to maintain the condition of the skin and to reduce skin cancer risk.

The topically active pharmaceutical or cosmetic composition should be applied in an amount effective to effect the desired changes in the skin. As used herein, "amount effective" shall mean an amount sufficient to cover the region of skin surface where preventing cancer, inhibiting the growth rate of a cutaneous tumor, or reducing the risk of cancer is desired. Preferably, the composition is applied to the skin surface such that, based upon a $cm^2$ of skin surface, from about 2 $\mu l/cm^2$ to about 500 $\mu l/cm^2$ of topically active agent is present when preventing cancer, inhibiting the growth rate of a cutaneous tumor, or reducing the risk of cancer is desired.

The following examples are provided to describe the invention in further detail. These examples are provided for illustrative purposes only, and are not to be construed as limiting the invention.

EXAMPLE 1

Soymilk Reduces UVB-Induced Tumorigenesis

Female SKH-1 mice, 6-7 weeks old, were purchased from Charles River Laboratories (Kingston, N.Y.) and were housed for at least one week before use. Mice were given water and Purina Laboratory Chow 5001 diet (Ralston-Purina, St. Louis, Mo.) ad libitum . Animal care was based on the "Guide for the Care and Use of Laboratory Animals", NIH Publication No. 85-23. Ultraviolet B light (UVB) lamps (FS72T12-UVB-HO) were from National Biological Corp. (Twinsburg, Ohio). Mice were irradiated with UV lamps that emit both UVB (280-320 nm, 75-80% of total energy) and UVA (320-375 nm, 20-25% of total energy). The UVB dose was quantified with a Spectra 305 dosimeter from DaevIin Co. (Byran, Ohio). The radiation was further calibrated with a Research radiometer/photometer model IL1700 from International Light Inc. (Newburgport, Mass.).

Mice were irradiated with UVB light (30 $mJ/cm^2$) for 25 to 30 seconds twice a week for 20 weeks. UVB irradiation was stopped when the first tumor was visible on the back of one mouse. This mouse was removed, and the population was classified as "at high risk for skin tumor development." Three weeks later, mice with no tumors were randomized into groups of 30 mice. One group (the control) was not treated, and other groups were topically treated, once a day, five days a week, with 100 μl of test material. Agents tested in this example included STI and BBI, and either freshly prepared soymilk or freshly prepared soymilk that was heat denatured at 90° C. for 20 min. Controls include vehicle alone and an unrelated protein (BSA).

The number of skin tumors and tumor sizes were measured every three weeks, using the methods described in Lou et al., (Effects of oral administration of tea, decaffeinated tea, and caffeine on the formation and growth of tumors in high risk SKH-1 mice previously treated with ultraviolet B light. Nutrition and Cancer 33, p. 146-153, 1999). The results of these measurements are summarized in Table 1 and shown in FIGS. 1A-1C and FIGS. 2A and 2B. An increase in tumor volume per mouse during the 21 weeks of the treatment phase was observed in each treatment regimen. The daily treatment with heated soymilk did not affect the rate of increase in tumor volume per mouse relative to control. Surprisingly, daily treatment with fresh soymilk had a dramatic effect on tumor volume. Tumor growth was significantly slower, and final tumor volumes were reduced by a factor of two to three in the mice treated with fresh soymilk, relative to the untreated or heated soymilk treated mice. See FIG. 2C. Table 1 shows the effect of fresh soymilk on tumor progression as measured by several additional parameters. The percent of tumor-bearing mice was reduced following treatment with fresh soymilk, as were the number of tumors per mouse and the tumor volume per tumor.

FIGS. 1A-1C show the effects of treatment of BBI and STI on mice irradiated with UVB. Surprisingly, using STI alone had an unexpected and significant effect on tumor progression. See FIGS. 1A-1C. The dramatic difference in results produced by treatment with fresh soymilk versus heat denatured soymilk, see FIGS. 2A-2C, also points to STI as an active anti-tumor ingredient, since it is well known that STI is denatured by cooking, but heat alone will not denature BBI, nor does it affect phytoestrogens. FIGS. 4A-4C are three photographs showing a random group of mice from each treatment group. This figure clearly demonstrates the reduced tumorigenicity in the mice treated with fresh soymilk vs heated treated soymilk or water. Compare FIG. 4A with 4B or 4C. These data indicate that topical treatment with fresh soymilk reduces UVB-induced tumor growth and progression in a high risk, pre-exposed population. These data also suggest that some of the active(s) of fresh soymilk that are involved in the tumor growth reduction are heat sensitive.

TABLE I

Effects of Topical Applications of Soymilk, STI, BBI, and Caffeine on the Development of Skin Tumors in SKH-1 Mice Previously Treated with Ultraviolet B Light

| Week | Treatment | Number of mouse per group | Weight per mouse(g) | Percent of mice with tumors | Tumors per mouse | Tumor volume per tumor ($mm^3$) | Tumor volume per mouse ($mm^3$) |
|---|---|---|---|---|---|---|---|
| 0 | No treatment | 30/30 | 29.9 ± 0.5 | 0 | 0 | 0 | 0 |
|  | Water | 29/29 | 30.0 ± 0.3 | 0 | 0 | 0 | 0 |
|  | Soymilk | 30/30 | 29.9 ± 0.5 | 0 | 0 | 0 | 0 |
|  | Heated Soymilk | 30/30 | 30.0 ± 0.5 | 0 | 0 | 0 | 0 |
|  | Liposomes | 30/30 | 30.0 ± 0.4 | 0 | 0 | 0 | 0 |
|  | STI | 30/30 | 30.2 ± 0.4 | 0 | 0 | 0 | 0 |
|  | BBI | 30/30 | 30.1 ± 0.4 | 0 | 0 | 0 | 0 |
|  | BSA in liposomes | 30/30 | 30.1 ± 0.2 | 0 | 0 | 0 | 0 |
|  | Acetone | 30/30 | 30.1 ± 0.2 | 0 | 0 | 0 | 0 |
|  | Caffeine (1.2 mg) | 30/30 | 30.0 ± 0.2 | 0 | 0 | 0 | 0 |
| 6 | No treatment | 30/30 | 30.3 ± 0.4 | 47.7% | 0.7 ± 0.2 | 1.5 ± 0.7 | 1.1 ± 0.5 |
|  | Water | 29/29 | 30.4 ± 0.5 | 27.6% | 0.4 ± 0.2 | 0.5 ± 0.0 | 0.2 ± 0.1 |
|  | Soymilk | 30/30 | 29.9 ± 0.4 | 6.7% | 0.1 ± 0.0 | 0.5 ± 0.0 | 0 |
|  | Heated Soymilk | 30/30 | 30.4 ± 0.6 | 36.7% | 0.4 ± 0.1 | 1.1 ± 0.4 | 0.5 ± 0.2 |
|  | Liposomes | 30/30 | 30.0 ± 0.4 | 40.0% | 0.7 ± 0.2 | 2.0 ± 0.7 | 1.4 ± 0.6 |
|  | STI | 30/30 | 29.7 ± 0.5 | 16.7% | 0.2 ± 0.1 | 3.5 ± 1.9 | 0.8 ± 0.6 |
|  | BBI | 30/30 | 30.0 ± 0.5 | 30.0% | 0.4 ± 0.1 | 0.9 ± 0.3 | 0.3 ± 0.1 |
|  | BSA in liposomes | 30/30 | 30.3 ± 0.4 | 20.0% | 2.0 ± 0.1 | 2.5 ± 1.9 | 0.6 ± 0.5 |
|  | Acetone | 30/30 | 29.6 ± 0.4 | 36.7% | 0.7 ± 0.2 | 2.6 ± 0.9 | 1.9 ± 0.8 |
|  | Caffeine | 30/30 | 29.3 ± 0.4 | 16.7% | 0.2 ± 0.1 | 1.3 ± 0.7 | 0.2 ± 0.1 |
| 9 | No treatment | 30/30 | 30.5 ± 0.3 | 43.3% | 0.8 ± 0.2 | 3.3 ± 1.5 | 2.7 ± 1.3 |
|  | Water | 29/29 | 30.6 ± 0.5 | 48.3% | 1.0 ± 0.3 | 1.3 ± 0.3 | 1.3 ± 0.6 |
|  | Soymilk | 30/30 | 30.1 ± 0.4 | 20.0% | 0.2 ± 0.1 | 0.5 ± 0.0 | 0.1 ± 0.0 |
|  | Heated Soymilk | 30/30 | 30.3 ± 0.5 | 46.7% | 0.7 ± 0.1 | 4.8 ± 1.9 | 3.2 ± 1.3 |
|  | Liposomes | 30/30 | 30.2 ± 0.4 | 46.7% | 1.9 ± 0.5 | 1.7 ± 0.6 | 3.2 ± 1.2 |
|  | STI | 29/30 | 30.0 ± 0.4 | 41.4% | 0.9 ± 0.2 | 3.0 ± 1.4 | 2.6 ± 1.4 |
|  | BBI | 30/30 | 29.9 ± 0.5 | 27.6% | 0.6 ± 0.2 | 1.7 ± 0.8 | 1.0 ± 0.7 |
|  | BSA in liposomes | 30/30 | 30.5 ± 0.4 | 50.0% | 1.1 ± 0.3 | 2.7 ± 1.2 | 2.9 ± 1.4 |
|  | Acetone | 30/30 | 30.4 ± 0.5 | 60.0% | 1.4 ± 0.5 | 2.8 ± 0.9 | 4.0 ± 1.5 |
|  | Caffeine (1.2 mg) | 30/30 | 29.4 ± 0.4 | 13.3% | 0.2 ± 0.1 | 3.4 ± 2.2 | 0.7 ± 0.5 |
| 12 | No treatment | 30/30 | 30.4 ± 0.4 | 70.0% | 1.9 ± 0.3 | 2.8 ± 0.7 | 5.4 ± 1.7 |
|  | Water | 29/29 | 31.1 ± 0.5 | 58.6% | 1.9 ± 0.5 | 2.3 ± 0.5 | 4.4 ± 1.2 |
|  | Soymilk | 30/30 | 30.4 ± 0.4 | 40.0% | 0.7 ± 0.2 | 1.8 ± 0.4 | 1.2 ± 0.4 |
|  | Heated Soymilk | 30/30 | 30.2 ± 0.6 | 53.3% | 1.0 ± 0.2 | 14.4 ± 6.0 | 14.9 ± 6.3 |
|  | Liposomes | 30/30 | 30.0 ± 0.4 | 70.0% | 4.0 ± 0.9 | 4.4 ± 1.0 | 17.8 ± 5.2 |
|  | STI | 29/30 | 29.8 ± 0.5 | 46.7% | 1.9 ± 0.5 | 4.8 ± 1.3 | 9.4 ± 3.9 |
|  | BBI | 30/30 | 30.6 ± 0.4 | 50.0% | 1.5 ± 0.4 | 2.4 ± 0.8 | 3.7 ± 1.8 |
|  | BSA in liposomes | 30/30 | 30.4 ± 0.5 | 80.0% | 2.6 ± 0.6 | 3.5 ± 1.0 | 9.1 ± 3.1 |
|  | Acetone | 30/30 | 30.0 ± 0.4 | 80.0% | 4.5 ± 0.9 | 5.2 ± 1.0 | 23.4 ± 7.1 |
|  | Caffeine | 30/30 | 29.0 ± 0.3 | 50.0% | 1.3 ± 0.4 | 3.2 ± 0.8 | 4.0 ± 1.9 |
| 15 | No treatment | 30/30 | 30.6 ± 0.4 | 76.7% | 2.9 ± 0.5 | 5.8 ± 1.4 | 16.8 ± 5.7 |
|  | Water | 29/29 | 31.2 ± 0.4 | 82.8% | 3.5 ± 0.6 | 2.8 ± 0.6 | 9.7 ± 3.4 |
|  | Soymilk | 30/30 | 30.7 ± 0.3 | 46.7% | 1.1 ± 0.3 | 3.0 ± 0.8 | 3.4 ± 1.0 |
|  | Heated Soymilk | 30/30 | 30.6 ± 0.5 | 70.0% | 2.3 ± 0.4 | 10.1 ± 3.6 | 22.9 ± 7.9 |
|  | Liposomes | 30/30 | 29.6 ± 0.9 | 90.0% | 6.2 ± 1.1 | 7.5 ± 1.3 | 46.2 ± 13.2 |
|  | STI | 29/30 | 30.1 ± 0.4 | 55.2% | 3.1 ± 0.7 | 5.8 ± 2.1 | 17.8 ± 7.9 |
|  | BBI | 30/30 | 30.6 ± 0.5 | 66.7% | 2.2 ± 0.4 | 4.1 ± 0.8 | 9.0 ± 2.4 |
|  | BSA in liposomes | 30/30 | 30.5 ± 0.4 | 90.0% | 5.3 ± 0.8 | 4.0 ± 0.7 | 21.4 ± 6.6 |
|  | Acetone | 30/30 | 30.0 ± 0.3 | 83.3% | 6.6 ± 1.0 | 7.4 ± 1.3 | 48.3 ± 16.7 |
|  | Caffeine (1.2 mg) | 30/30 | 29.4 ± 0.3 | 56.7% | 2.1 ± 0.5 | 3.2 ± 0.6 | 6.7 ± 2.2 |
| 18 | No treatment | 30/30 | 31.6 ± 0.4 | 83.3% | 4.2 ± 0.6 | 9.0 ± 2.0 | 38.0 ± 12.8 |
|  | Water | 28/29 | 32.0 ± 0.5 | 96.6% | 5.4 ± 0.6 | 4.0 ± 1.3 | 21.5 ± 7.5 |
|  | Soymilk | 30/30 | 30.7 ± 0.4 | 66.7% | 1.9 ± 0.5 | 6.5 ± 1.8 | 12.3 ± 4.6 |

TABLE I-continued

Effects of Topical Applications of Soymilk, STI, BBI, and Caffeine on the Development of Skin Tumors in SKH-1 Mice Previously Treated with Ultraviolet B Light

| Week | Treatment | Number of mouse per group | Weight per mouse(g) | Percent of mice with tumors | Tumors per mouse | Tumor volume per tumor (mm$^3$) | Tumor volume per mouse (mm$^3$) |
|---|---|---|---|---|---|---|---|
| | Heated Soymilk | 30/30 | 31.0 ± 0.6 | 83.3% | 4.1 ± 0.7 | 6.9 ± 2.4 | 28.7 ± 9.8 |
| | Liposomes | 30/30 | 30.9 ± 0.5 | 90.0% | 7.1 ± 1.0 | 8.7 ± 1.1 | 61.7 ± 15.0 |
| | STI | 28/30 | 30.0 ± 0.4 | 63.3% | 4.2 ± 0.9 | 7.3 ± 2.2 | 30.7 ± 11.9 |
| | BBI | 30/30 | 30.7 ± 0.5 | 76.7% | 3.2 ± 0.6 | 5.9 ± 1.3 | 19.0 ± 4.6 |
| | BSA in liposomes | 30/30 | 30.9 ± 0.5 | 90.0% | 6.5 ± 0.9 | 6.3 ± 1.0 | 41.1 ± 9.7 |
| | Acetone | 29/30 | 30.7 ± 0.5 | 86.7% | 6.9 ± 1.0 | 8.4 ± 1.3 | 57.4 ± 13.7 |
| | Caffeine | 30/30 | 29.6 ± 0.4 | 80.0% | 3.6 ± 0.6 | 6.2 ± 1.3 | 22.1 ± 6.2 |
| 21 | No treatment | 30/30 | 31.5 ± 0.3 | 100.0% | 5.9 ± 0.7 | 8.8 ± 2.1 | 51.9 ± 16.3 |
| | Water | 28/29 | 32.0 ± 0.4 | 96.6% | 6.3 ± 0.6 | 6.4 ± 2.4 | 40.6 ± 15.6 |
| | Soymilk | 30/30 | 31.1 ± 0.3 | 83.3% | 2.7 ± 0.5 | 4.8 ± 1.3 | 12.9 ± 4.4 |
| | Heated Soymilk | 29/30 | 31.3 ± 0.6 | 90.0% | 6.7 ± 0.9 | 8.9 ± 3.2 | 59.9 ± 20.9 |
| | Liposomes | 30/30 | 30.9 ± 0.4 | 96.7% | 8.2 ± 1.1 | 9.0 ± 1.5 | 73.7 ± 15.0 |
| | STI | 28/30 | 30.6 ± 0.4 | 80.0% | 5.6 ± 0.9 | 8.6 ± 3.2 | 48.7 ± 23.3 |
| | BBI | 30/30 | 30.8 ± 0.4 | 90.0% | 4.5 ± 0.6 | 7.4 ± 2.0 | 33.2 ± 9.6 |
| | BSA in liposomes | 30/30 | 30.7 ± 0.4 | 90.0% | 7.1 ± 0.8 | 6.3 ± 1.0 | 44.7 ± 11.6 |
| | Acetone | 28/30 | 30.5 ± 0.4 | 90.0% | 6.9 ± 0.9 | 9.6 ± 2.0 | 65.7 ± 0.9 |
| | Caffeine | 30/30 | 29.9 ± 0.3 | 76.7% | 4.0 ± 0.7 | 5.3 ± 1.0 | 21.5 ± 6.0 |

SKH-1 mice (7-8 weeks old) were treated with ultraviolet B light (UVB; 30 mJ/cm$^2$) twice weekly for 20 weeks and UVB treatment was stopped. Three weeks later, the mice (with no visible tumors) were randomized into 10 groups (30 mice per group) and the mice were treated topically:
group 2, 100 ul water;
group 3, 100 ul Soymilk;
group 4, 100 ul heated Soymilk;
group 5, 100 ul liposomes;
group 6, trypsin inhibitor (STI; 0.8 mg; T9003, Sigma) in 100 ul liposomes;
group 7, Bowman-Birk protease inhibitor (BBI; 0.8 mg; T97770, Sigma) in 100 ul liposomes;
group 8, bovine serum albumin (BSA; 0.8 mg) in 100 ul liposomes;
group 9, 100 ul acetone;
group 10, caffeine, CAF; 1.2 mg) in 100 ul acetone once a day 5 days per week for 21 weeks.

EXAMPLE 2

Caffeine Reduces UVB-Induced Tumorigenesis

The experiment described in Example 1 was also performed using a topical caffeine treatment. Caffeine was purchased from Sigma (St. Louis, Mo.). Acetone was from Fisher Scientific (Springfield, N.J.). Mice were treated daily, five days a week with caffeine (1.2 mg) in 100 μl acetone or with 100 μl of acetone only. Experimental procedures and measurements were identical to those described in Example 1, and the two experiments were performed at the same time, using the same UVB-irradiated population.

Figure 5A:
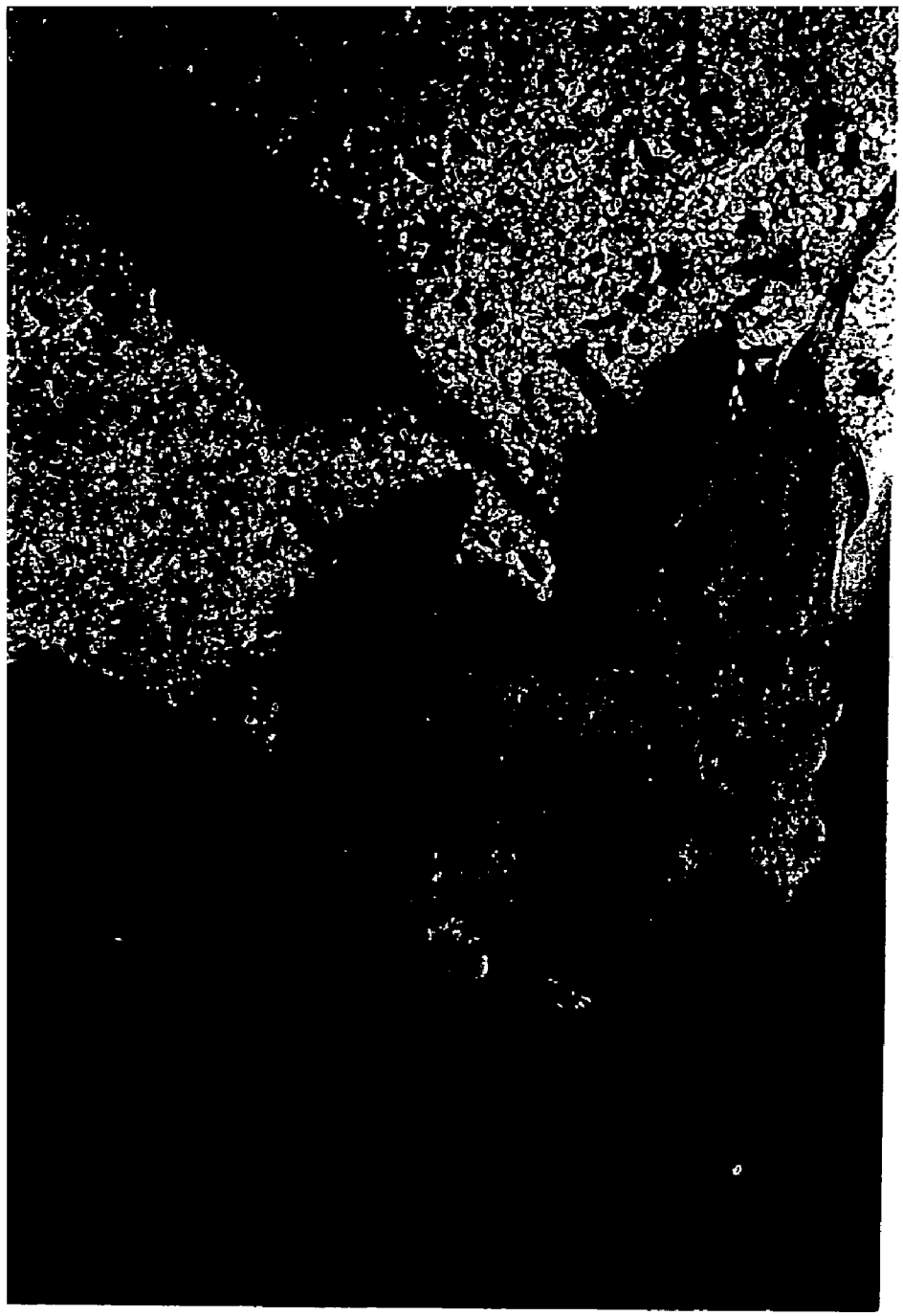
FIGS. 5A and 5B are a pair of photographs showing the reduction in size and number of UV-induced tumors among mice treated topically with a solution of caffeine in acetone (FIG. 5B) compared to mice treated with acetone alone (FIG. 5A).
Figure 5B:
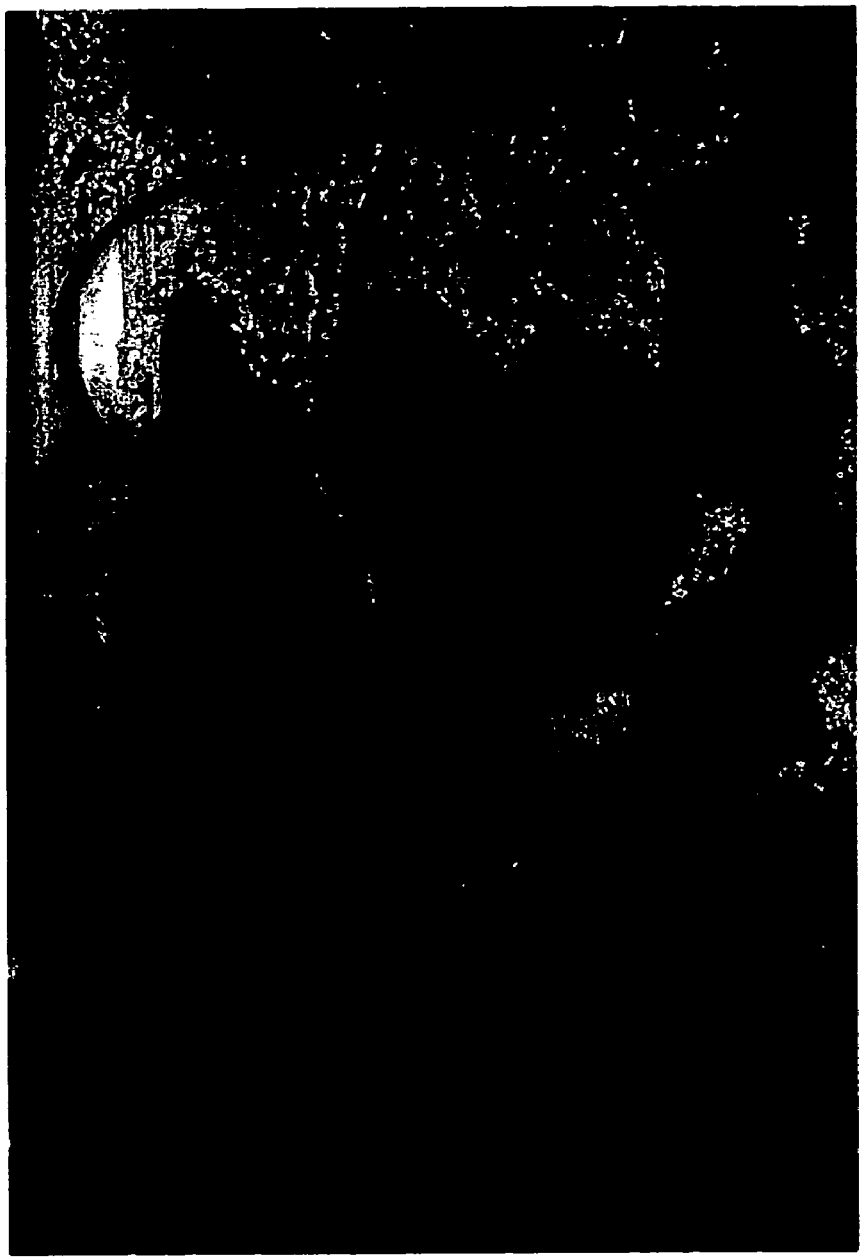

FIGS. 3A-3C show that tumor progression following acetone treatment was very similar to that of the untreated group graphed in FIG. 2. The caffeine treated mice showed a marked delay in tumor progression, as evident from the tumor volume per mouse data in FIG. 3C. The additional parameters reported in Table 1 further support this observation of the beneficial effect of caffeine on tumor progression. The percentage of tumor-bearing bearing mice was reduced following caffeine treatment, as were the number of tumors per mouse and the tumor volume per tumor. FIGS. 5A and 5B are two pictures, each depicting a random group of mice from acetone treated (FIG. 5A) vs. caffeine treated (FIG. 5B mice). This figure clearly demonstrates the reduced tumorigenicity in the caffeine-treated mice.

EXAMPLE 3

Preparation of Soymilk from Soybean Powder 160 g of soybean powder (Sunlight Foods, Taipei, Taiwan) was added to about 1440 g of deionized water. The mixture was stirred at room temperature for about 1 hour. The mixture was then filtered through a sieve having holes of 75 μm diameter. The filtrate resulted in about 1.1 kg of soymilk.

EXAMPLE 4

Preparation of Soymilk Gel from Soymilk

The following compositions of this invention were prepared as follows. The weight percentages of each ingredient in the compositions are indicated below in Table 2 and Table 3. First, the soymilk, as prepared in example 3, was placed into a first beaker. The preservative Phenonip® (a mixture of the preservatives methyl-paraben, propyl-paraben, ethyl-paraben, and phenoxy-ethanol sold by NIPA, Wilmington, Del.) or the preservative phenoxyethanol were added to the soymilk. Next, the chelating agent Disodium EDTA and in some examples the humectant glycerin were added to the first beaker and mixed with the soymilk. It is also possible to further add cyclomethicone, or dimethicone (tradename Dow Corning 200 Fluid ®), or PolySorbate 20, or Aluminum Starch Octyl Succinate, or Sucrose Cocoate, or PEG-6 Capric/Caprylic Triglycerides to the soymilk mixture at this step as required in some examples in Table 2 and Table 3. A mixture of the thickener polyacrylamide, laureth-7, and C13-14 isoparaffins (sold by Seppic, Paris, France under the Tradename Sepigel®) was added to a second beaker along with the anti-oxidant BHT. The ingredients in the second beaker were then added to the ingredients of the first beaker and mixed until homogenous.

TABLE 2

Soybean Essence formulations

|  | 24 | 26 | 27 | 28 | 33 | 34 | 35 |
|---|---|---|---|---|---|---|---|
| Soymilk | 94.40% | 92.40% | 90.70% | 94.70% |  |  |  |
| Phenoxyethanol and Parabens | 1.00% | 1.00% | 1.00% | 1.00% | 1.00% | 1.00% | 1.00% |
| Glycerin |  |  | 5.00% |  |  |  |  |
| Disodium EDTA | 0.05% | 0.05% | 0.05% | 0.05% | 0.05% | 0.05% | 0.05% |
| Polyacrylamide/Laureth-7/$C_{13-14}$ Isoparrafin | 3.50% | 3.50% | 3.20% | 3.20% | 3.20% | 3.20% | 3.20% |
| Ascorbic Acid |  | 1.00% |  |  |  |  |  |
| Butylated Hydroxytoluene | 0.05% | 0.05% | 0.05% | 0.05% | 0.05% | 0.05% | 0.05% |
| Deionized Water |  |  |  |  | 90.70% | 90.70% | 85.70% |
| Lactoferrin | 1.00% | 1.00% |  |  |  |  |  |
| Tocopherol |  | 1.00% |  |  |  |  |  |
| Dow Corning 200 Fluid |  |  |  | 1.00% |  |  |  |
| Soymilk Powder |  |  |  |  | 5.00% |  |  |
| Soybean Extract using Ethanol/Water Mixture |  |  |  |  |  | 5% | 10% |
| TOTAL | 100% | 100% | 100% | 100% | 100% | 100% | 100% |

TABLE 3

Soybean Essence formulations
Soybean Essences

|  | 1 | 6 | 8 | 21 | 23 |
|---|---|---|---|---|---|
| Soymilk | 87.42% | 89.04% | 96.09% | 96.05% | 95.70% |
| Phenoxyethanol | 0.73% |  |  |  |  |
| Phenoxyethanol and Parabens |  | 1.00% | 1.00% | 1.00% | 1.00% |
| Glycerin | 2.50% | 2.50% |  |  |  |
| Cyclomethicone | 2.00% |  |  |  |  |
| Aluminum Starch Ocetyl Succinate | 0.75% |  |  |  |  |
| Sucrose Cocoate | 1.00% | 1.00% |  |  |  |
| PEG-6 Capric/Caprylic Triglycerides | 3.00% | 3.00% |  |  |  |
| Disodium EDTA | 0.10% | 0.10% |  |  | 0.05% |
| Polyacrylamide/Laureth-7/$C_{13-14}$ Isoparrafin | 2.50% | 2.75% | 2.90% | 2.90% | 3.20% |
| Ascorbic Acid |  | 0.01% |  |  |  |
| Butylated Hydroxytoluene |  | 0.10% | 0.01% | 0.05% | 0.05% |
| Polysorbate 20 |  | 0.50% |  |  |  |
| TOTAL | 100% | 100% | 100% | 100% | 100% | with the anti-oxidant BHT. The ingredients in the second beaker were then added to the ingredients of the first beaker and mixed until homogenous. The anti-oxidants ascorbic acid, sodium ascorbyl phosphate, lactoferrin, or tocopherol were then added to the beaker and homogeneously mixed to form the resulting gel.

EXAMPLE 5

Preparation of Soymilk Gel from Soybean Powder, Soymilk Powder or Soybean Extract The following compositions of this invention were prepared as follows. The weight percentage of each ingredient in each of the preparations is indicated below in Table 3. First, the soymilk powder (Devansoy Farms, Carroll, Iowa) or the soybean powder (Sunlight Foods, Taipei, Taiwan) or the Soybean Extract and deionized water were placed into a first beaker and mixed to reconstitute the soy powder. The preservative Phenonip® and the chelating agent Disodium EDTA were then added to the first beaker and mixed with the soymilk. A mixture of polyacrylamide, laureth-7, and C13-14 isoparaffins was added to a second beaker along with the While certain preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting the progression of a cutaneous tumor comprising topical application of at least one composition containing a non-denatured, Kunitz-type soybean trypsin inhibitor in an amount of from about 0.01-99% by weight.

2. The method of claim 1, wherein said composition is applied at least once daily on a continuous basis.

3. The method of claim 1, wherein said composition is applied at least twice daily for at least eight weeks and at least once daily on a continuous basis thereafter.

4. The method of claim 1, wherein said composition comprises 0.1-10% by weight of said non denatured soybean trypsin inhibitor and is applied for at least about four to about ten weeks followed by topical application of a composition comprising 0.01-10% by weight of said non denatured soybean trypsin inhibitor on a daily basis thereafter.

5. The method of claim 1, wherein said non-denatured soybean trypsin inhibitor is contained within liposomes suspended in a cosmetically acceptable carrier.

6. The method of claim 4, wherein said non-denatured soybean trypsin inhibitor is contained within liposomes suspended in a cosmetically acceptable carrier.

7. The method of claim 1, wherein said composition further comprises a cosmetically acceptable vehicle.

8. The method of claim 1, wherein said composition further comprises at least one anti-inflammatory agent.

9. The method of claim 1 wherein said composition further comprises at least one anti-cancer agent.

10. The method of claim 1, wherein said composition further comprises at least one anti-oxidant.

11. The method of claim 1, wherein said composition further comprises at least one sunscreen.

12. The method of claim 1, wherein said composition further comprises from about 0.1 to about 20% emulsifier, and a preservative in an effective amount.

13. The method of claim 12, wherein said composition further comprises an anti-oxidant.

14. The method of claim 12, wherein said composition further comprises an anti-cancer agent.

15. The method of claim 12, wherein said composition further comprises at least one compound selected from the group consisting of anti-oxidants, sunscreens, moisturizers, bleaching agents, depigmentation agents, darkening agents, surfactants, foaming agents, conditioners, humectants, fragrances, anti-aging agents, anti-inflammatory agents, and anti-cancer agents.

* * * * *